United States Patent
DeSimas et al.

(10) Patent No.: US 10,761,054 B2
(45) Date of Patent: Sep. 1, 2020

(54) SYSTEMS AND METHODS FOR AUTOMATED ALIGNMENT, CALIBRATION AND STANDARDIZATION OF ELECTROPHORESIS DATA

(71) Applicant: Agilent Technologies, Inc., Santa Clara, CA (US)

(72) Inventors: Bruce DeSimas, Danville, CA (US); Boris Belopolski, New Canaan, CT (US)

(73) Assignee: Agilent Technologies, Inc., Santa Clara, CA (US)

( * ) Notice: Subject to any disclaimer, the term of this patent is extended or adjusted under 35 U.S.C. 154(b) by 255 days.

(21) Appl. No.: 15/595,796

(22) Filed: May 15, 2017

(65) Prior Publication Data

US 2018/0052138 A1    Feb. 22, 2018

Related U.S. Application Data

(60) Provisional application No. 62/336,479, filed on May 13, 2016.

(51) Int. Cl.
| | |
|---|---|
| *G01N 27/447* | (2006.01) |
| *G16C 20/10* | (2019.01) |
| *G16C 20/80* | (2019.01) |
| *B01D 57/02* | (2006.01) |

(52) U.S. Cl.
CPC ....... *G01N 27/44717* (2013.01); *B01D 57/02* (2013.01); *G01N 27/447* (2013.01);
(Continued)

(58) Field of Classification Search
CPC ......... G01N 27/44791; G01N 27/4473; G01N 27/44717
See application file for complete search history.

(56) References Cited

U.S. PATENT DOCUMENTS

| | | |
|---|---|---|
| 6,430,512 B1 | 8/2002 | Gallagher |
| 2005/0115837 A1* | 6/2005 | Burgi ............... G01N 27/44704 204/452 |

(Continued)

FOREIGN PATENT DOCUMENTS

JP        11-248679 A  *  9/1999  ........... G01N 27/447

OTHER PUBLICATIONS

Akbari et al., "Adaptive weighted least squares method for the estimation of DNA fragment lengths from agarose gels," Electrophoresis 2002, 23, 176-181 (Year: 2002).*

(Continued)

*Primary Examiner* — Alexander S Noguerola

(57) ABSTRACT

Systems and methods are provided for improving the analysis of analytes by using electrophoresis apparatus. Exemplary methods provide an increase in the yield of useful results, e.g., quantity and quality of useable data, in automated peak detection, in connection with an electrophoretic separation, e.g., capillary electrophoresis. In various embodiments, the system virtualizes the raw data, transforming the migration time into virtual units thereby allowing the visual comparison of analyte electropherograms and the reliable measurement of unknown analytes. The analytes can be, for example, any organic or inorganic molecules, including but not limited to nucleic acids (DNA, RNA), proteins, peptides, glycans, metabolites, secondary metabolites, lipids, or any combination thereof. Analyte detection can be performed by any method including, but not limited to, fluorescence detection or UV absorption. The present teachings provide, among other things, for consistent comparisons of analyte peaks across samples, across instruments, across runs, and across migration times.

20 Claims, 20 Drawing Sheets

(52) U.S. Cl.
CPC ... *G01N 27/4473* (2013.01); *G01N 27/44726* (2013.01); *G01N 27/44791* (2013.01); *G16C 20/10* (2019.02); *G16C 20/80* (2019.02)

(56) References Cited

U.S. PATENT DOCUMENTS

2007/0112534 A1    5/2007    Jaeger
2009/0288951 A1    11/2009    Rapp et al.

OTHER PUBLICATIONS

Vern Winston, "Use of a polynomial exponential function to describe migration of proteins on sodium dodecyl sulfate-polyacrylamide gels," Electrophoresis 1989, 10, 220-222 (Year: 1989).*

JPO English langauge translation of JP 11-248679 A (Year: 1999).*

O'Shea et al., "High resolution slab gel electrophoresis of 8-amino-1.3.6-pyrenetrisulfonic acid (ATPS) tagged oligosaccharides using a DNA sequencer," Electrophoresis 1996, 17, 681-688 (Year: 1996).*

ABI Prism® 373 DNA Sequencer with XL Upgrade User's Manual (Year: 2001).*

Beckman P/ACE™ MDQ User's Guide (Year: 2009).*

Mittermayr, Stephan, et al.; Influence of molecular configuration and conformation on the electromigration of oligosaccharides in narrow bore capillaries; Electrophoresis 2012, vol. 33, pp. 1000-1007.

Jarvas, Gabor, et al.; Triple-Internal Standard Based Glycan Structural Assignment Method for Capillary Electrophoresis Analysis of Carbohydrates; Analytical Chemistry 2016, vol. 88, pp. 11364-11367.

Supplementary Partial European Search Report, dated Dec. 17, 2019, issued in European Application No. EP17797032.

* cited by examiner

SYSTEMS AND METHODS FOR AUTOMATED ALIGNMENT, CALIBRATION AND STANDARDIZATION OF ELECTROPHORESIS DATA

FIELD

The present teachings relate to automated methods for standardizing electrophoresis instruments to produce aligned data useful, for example, in analyte screening, research, qualitative or quantitative measurements and diagnostics uses.

BACKGROUND

Capillary electrophoresis (CE) has been utilized as an analytical technique, e.g., in the fields of life sciences, biological sciences, and pharmaceuticals, for many years. (See, e.g., YAN XU, Cleveland State University, The Chemical Educator, Tutorial: Capillary Electrophoresis, 1/Vol. 1, No. 2, 1996, Springer-Verlag New York, Inc.; incorporated herein by reference in its entirety.) Even today, however, the use of electrophoresis data in analyte measurements can often be difficult and time consuming. In many cases, scientists and engineers must manually adjust the raw electrophoresis data before peak integration and eventual detection of analytes or mixtures of analytes. A notorious challenge in the field is related to the nature of the variability in the data from the electrophoresis separation process and the instrumentation detection systems. It is well known that data from run-to-run or instrument-to-instrument can vary in migration time to a degree that can render the data unfit for either qualitative or quantitative analysis of analytes. A generally desirable goal of measuring analyte mixtures is the ability to build a standard library of characterized analytes, characterized, for example, by mass spectrometry, and then use the library against which to compare known analytes.

SUMMARY

A non-limiting summary of various aspects of the present teachings, in accordance with various embodiments, is provided next.

Various aspects of the present teachings provide systems and methods for standardization (virtualization) of electrophoretic data used, for example, in analyte detection and quantification. Various embodiments of the present teachings provide, for example, a method of performing partial or full alignment in electrophoresis apparatus. According to various embodiments, for example, the method can comprise steps such as the following:
(i) Combining raw separation data with electric current and optionally, electric potential data collected during the separation process in such a way that the resulting separation data curve can be aligned with one or more reference separation curves;
(ii) Increasing or decreasing the time value for every point of the original separation data depending on the value of the electric current at that point; and,
(iii) Optionally and in addition, increasing or decreasing the time value for every point of the original separation data depending on the value of the electric potential at that point.

Further aspects of the present teachings relate to methods and apparatus for increasing the yield of useful results in automated peak detection.

In various embodiments, a method for increasing the yield of useful results in automated peak detection can comprise, for example:
(i) Measuring electrical current in a separation channel,
(ii) Electrophoresing a sample including one or more unknown analytes along the channel,
(iii) Optically detecting for the one or more analytes at a detection zone of the channel,
(iv) Collecting detected signal data, and
(v) Processing the collected signal data via a method that uses the measured current.

In various embodiments, the processing of step (v) can comprise, for example, correcting for problematic issues in the data during peak detection.

Various aspects of the present teachings relate to an improved system for analyzing a sample comprising one or more unknown analytes using electrophoretic separation. The system can comprising, for example:
(a) a separation channel comprising a separation medium,
(b) a power source for applying a potential across the channel to cause a sample to migrate there along,
(c) a detector for measuring signal intensity associated with a sample migrating along the channel as a function of time;
(d) a computing portion comprising a computer-readable medium containing software code embodying executable instructions for:
(i) receiving a first set of data comprising a plurality of signal peaks over time corresponding to an electrophoretic separation of a known ladder standard,
(ii) allocating respective standardized values, expressed in virtual units, for the peak-migration times,
(iii) fitting a polynomial curve to the ladder standard, thereby generating a first polynomial model,
(iv) determining an offset from the origin in the first polynomial model,
(v) translating the first polynomial model, using the offset, to pass through the origin, thereby generating a translated first polynomial model,
(vi) recycling the first data set back through the first polynomial model and determining at least two prediction residuals, wherein the residuals reveal the extent of mismatch, in time, between the received and modelled peaks,
(vii) fitting a cubic spline curve to the residuals, thereby generating a cubic-spline model component,
(viii) receiving a second set of data comprising one or more peaks over time corresponding to an electrophoretic separation of a mixture comprising (a) an unknown analyte, (b) an upper bracketing standard, and (c) a lower bracketing standard,
(ix) determining a peak for the upper bracketing standard,
(x) adjusting the slope and curvature of the translated first polynomial model in equal proportions to the upper bracketing standard, thereby generating an upper bracketing standard model,
(xi) determining a peak for the lower bracketing standard using the upper bracketing standard model,
(xii) fitting a polynomial curve to the lower bracketing standard, the upper bracketing standard, and the origin, thereby generating a second polynomial model,
(xiii) combining (a) the second polynomial model, (b) the cubic spline model component, and (c) the offset, thereby generating a final reference model, and
(xiv) transforming the second set of data into virtual units using the final reference model; and
(e) a processor to execute the computer-readable code on the computer-readable medium.

In various embodiments, the separation channel comprises a longitudinal bore of an elongate capillary tube.

According to various embodiments, the polynomial curves comprise fourth- or lower-order polynomial curves. For example, a quadratic polynomial can be employed.

In various embodiments, the known ladder standard comprises dextran and the virtual units comprise glucose units.

Various aspects of the present teachings relate to an improved system for analyzing a sample comprising an unknown analyte using electrophoretic separation, wherein the system comprises:

(a) a separation channel comprising a separation medium,
(b) a power source for applying a potential across the channel to cause a sample to migrate there along,
(c) a detector for measuring signal intensity associated with a sample migrating along the channel as a function of time; and
(d) a computing portion comprising a computer-readable medium containing software code embodying executable instructions for:
(i) receiving a first set of data comprising a plurality of signal peaks over time corresponding to an electrophoretic separation of a known ladder standard,
(ii) allocating respective standardized values, expressed in virtual units, for the peak-migration times,
(iii) fitting a polynomial curve to the ladder standard, thereby generating a first polynomial model,
(iv) determining an offset from the origin in the first polynomial model,
(v) translating the first polynomial model, using the offset, to pass through the origin, thereby generating a translated first polynomial model,
(vi) receiving a second set of data comprising one or more peaks over time corresponding to an electrophoretic separation of a mixture comprising (a) one or more respective unknown analytes,
(b) an upper bracketing standard, and (c) a lower bracketing standard,
(vii) determining a peak for the upper bracketing standard,
(viii) adjusting the slope and curvature of the translated first polynomial model in equal proportions to the upper bracketing standard, thereby generating an upper bracketing standard model,
(ix) determining a peak for the lower bracketing standard using the upper bracketing standard model,
(x) fitting a polynomial curve to (a) the upper bracketing standard, (b) the lower bracketing standard, and (c) the origin, thereby generating a second polynomial model,
(xi) combining the second polynomial model and the offset, thereby generating a final reference model, and
(xii) transforming the second set of data into virtual units using the final reference model.

In various embodiments, the polynomial curves comprise fourth- or lower-order polynomial curves.

According to various embodiments, the known ladder standard comprises dextran and the virtual units comprise glucose units.

Further aspects of the present teachings relate to a method for performing an alignment on sample data from a separation using an electrophoresis apparatus. For example, the method can comprise the steps:
(i) applying a potential across a separation channel to generate a current therein and to separate a sample comprising an unknown analyte in the channel so that an electropherogram of a signal as a function of time is produced; (ii) during the separation, measuring the current between the ends of the channel as a function of time; (iii) integrating the current with respect to time to provide a cumulative current as a function of time; (iv) using a reference standard, constructing a reference model that relates cumulative current values to migration time values; and (v) using the reference model, adjusting observed migration time values for the sample to current-normalized time values; whereby the electropherogram for the sample is aligned.

According to various embodiments, the method further comprises identifying peaks in the electropherogram that correlate with the unknown analyte in the sample.

In accordance with various embodiments, a quadratic polynomial fit is used to construct the reference model.

In various embodiments, the method also comprises: further aligning the current-normalized time values from step (v) using one or more additional reference models that relate the current-normalized time values to standardized virtual units.

According to various embodiments, the one or more additional reference models are constructed using a ladder standard and at least one bracketing standard.

Additional aspects of the present teachings relate to a method for aligning data from an electrophoretic separation of a sample mixture.

In various embodiments, for example, the method can comprise the steps: (a) performing an initial alignment on raw sample data using a first reference model that relates peak-migration time values to cumulative current values, and (b) performing a second alignment on the data aligned in step (a) using one or more additional reference models that relate the data aligned in step (a) to standardized virtual units.

According to various embodiments, the one or more additional reference models are constructed using a ladder standard and at least one bracketing standard.

In various embodiments, the bracketing standard comprises a portion of the sample mixture.

In accordance with various embodiments, the second reference model is constructed using an upper bracketing standard. In some embodiments, the second reference model is constructed further using a lower bracketing standard.

Still further aspects of the preset teachings relate to a non-transitory computer readable product embodying a set of instructions for execution by a computer to analyze one or more analytes of a sample mixture separated using an electrophoretic apparatus. In various embodiments, for example, the program can comprise code for:
(i) receiving a first set of data comprising a plurality of signal peaks over time corresponding to an electrophoretic separation of a known ladder standard,
(ii) allocating respective standardized values, expressed in virtual units, for the peak-migration times,
(iii) fitting a polynomial curve to the ladder standard, thereby generating a first polynomial model,
(iv) determining an offset from the origin in the first polynomial model,
(v) translating the first polynomial model, using the offset, to pass through the origin, thereby generating a translated first polynomial model,
(vi) recycling the first data set back through the first polynomial model and determining at least two prediction residuals, wherein the residuals reveal the extent of mismatch, in time, between the received and modelled peaks,
(vii) fitting a cubic spline curve to the residuals, thereby generating a cubic-spline model component,
(viii) receiving a second set of data comprising one or more peaks over time corresponding to an electrophoretic separation of a mixture comprising (a) an unknown analyte, (b) an upper bracketing standard, and (c) a lower bracketing standard, (ix) determining a peak for the upper bracketing standard,
(x) adjusting the slope and curvature of the translated first polynomial model in equal proportions to the upper bracketing standard, thereby generating an upper bracketing standard model,
(xi) determining a peak for the lower bracketing standard using the upper bracketing standard model,
(xii) fitting a polynomial curve to the lower bracketing standard, the upper bracketing standard, and the origin, thereby generating a second polynomial model,
(xiii) combining (a) the second polynomial model, (b) the cubic spline model component, and (c) the offset, thereby generating a final reference model, and
(xiv) transforming the second set of data into virtual units using the final reference model.

These and other objects and features of the present teachings will be more fully appreciated when the following description is read in conjunction with the accompanying drawings.

BRIEF DESCRIPTION OF THE FIGURES

Various embodiments of the disclosure will be discussed with reference to the following exemplary and non-limiting illustrations, in which like elements are numbered similarly, and where.

DESCRIPTION

Reference will now be made to various embodiments. While the present teachings will be described in conjunction with various embodiments, it will be understood that they are not intended to limit the present teachings to those embodiments. On the contrary, the present teachings are intended to cover various alternatives, modifications, and equivalents, as will be appreciated by those of skill in the art.

Figure 1:
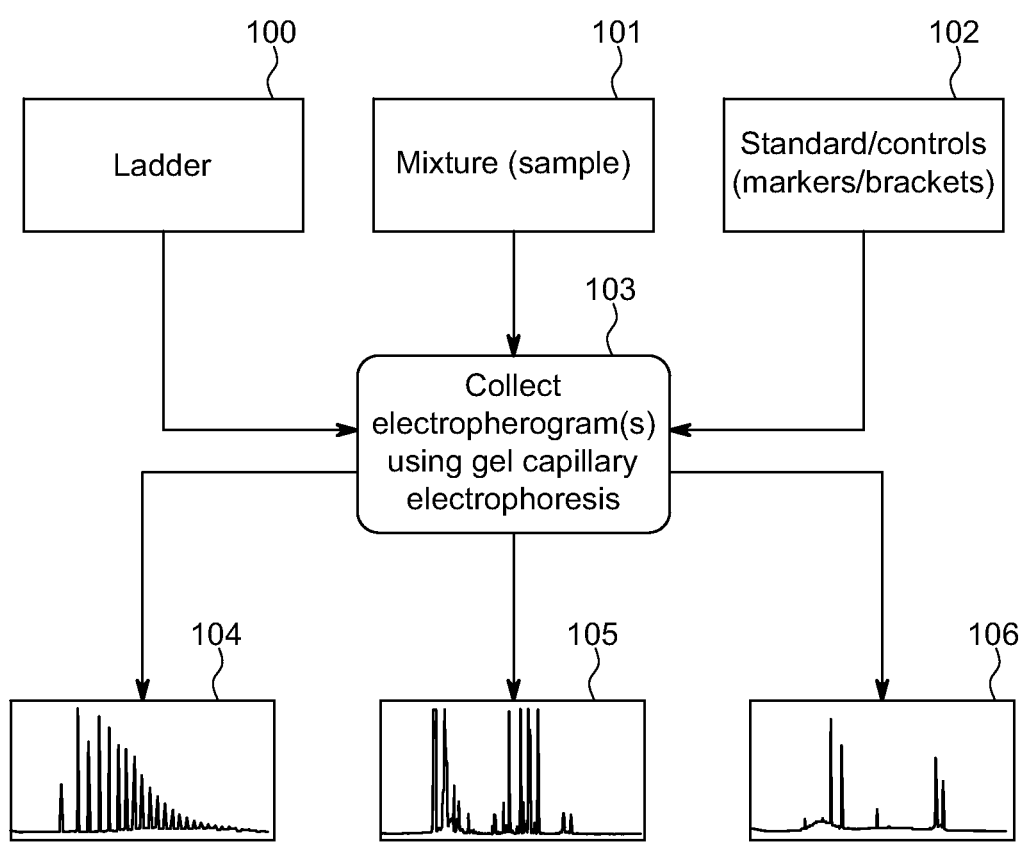
FIG. 1 Illustrates the collection of raw electrophoresis data collection; according to various embodiments.

In accordance with various embodiments, FIG. 1 provides a block diagram of an exemplary data collection system and shows the use of a fluorescent macromolecular ladder 100, unknown analyte mixture (sample) 101, and standards/controls used as markers or brackets in analysis. In various embodiments, such analytes can have an appropriate fluorescent dye label attached to the analyte such that the fluorescent dye can be detected in an electrophoresis apparatus, or system. Any one of a variety of types of known electrophoresis apparatus can be employed. In various embodiments, an electrophoresis apparatus is utilized comprising one or more elongate separation channels, such as capillaries, into which samples can be injected and electrophoretically separated.

In various embodiments, for example, an electrophoretic separation can be performed by applying a potential across along one or more separation channels, each defined by a respective elongate bore extending longitudinally along the length of a capillary tube. One or more unknown analytes, in respective samples, can be injected into the one or more respective capillaries for separation and detection. A suitable separation, or sieving, matrix or polymer can fill each capillary, e.g., a stationary or in-situ gel or polymer latticework, or a flowable polymer formulation. The samples can then be electrophoresed such that the samples migrate along their respective separation channels in a manner providing for separation of the one or more analytes. An energy source, such as a laser or LED, can be configured to direct an excitation beam at a detection zone, or window, at a defined location along each capillary. The excitation beam can excite dyes associated with each of the one or more unknown analytes, such that they emit light. Emitted light from sample zones can then pass through one or more appropriate lens/filter arrangements (e.g., a collection lens, laser light filter, and a focusing lens), so that focused light is incident on a suitable detector, e.g., one or more photomultiplier tubes (PMTs) or charge-couple devices (CCD cameras), capable of detecting emissions from the detection zone. Electronic signals from the detector(s) can provide information about the character or sequence of the analyte sample.

Figure 2:
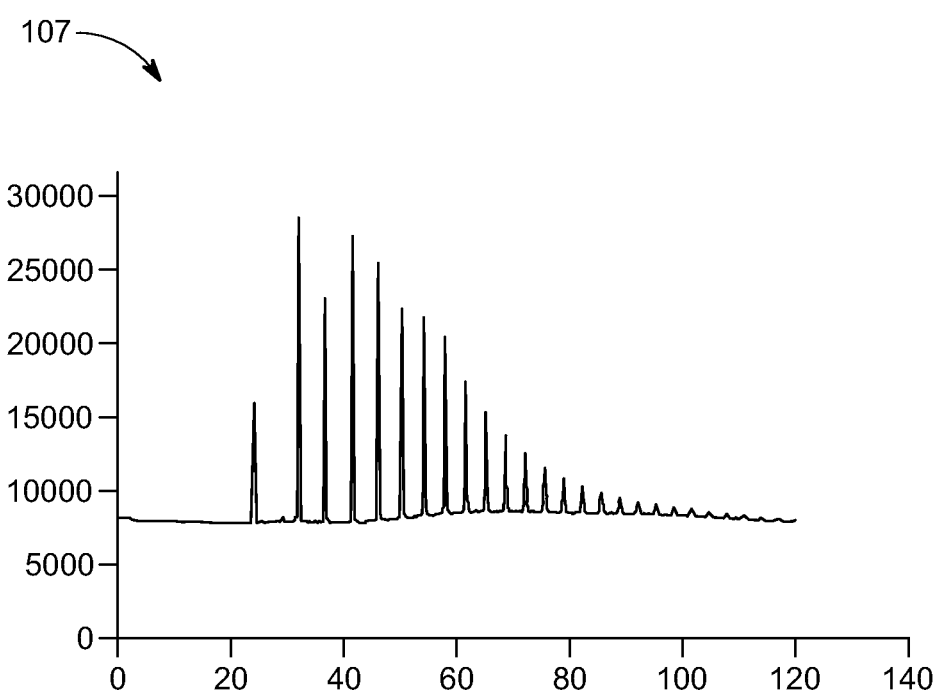
FIG. 2 Illustrates an electrophoretic trace from a typical separation using a capillary-electrophoresis apparatus; and, in particular, shows the migration of plural oligomers comprising a fluorescent macromolecular ladder, with fluorescence data shown on the y-axis and migration time in seconds shown on the x-axis; according to various embodiments.

Further in this regard, captured images can be converted to a readable form called an electropherogram, from which the presence or information about an analyte of interest can then be determined. An example of an electropherogram, also known as a trace or time-series plot, is shown in FIG. 2. The electropherogram of FIG. 2 is a graphical representation of sampled signal data, in the form of peaks, over time. In the depicted embodiments, the signal data is representative of a typical electrophoretic separation, or run, using a capillary electrophoresis apparatus. Particularly, FIG. 2 shows signals detected from the migration of plural oligomers comprising a fluorescent macromolecular ladder, with fluorescence data on the y-axis and migration time in seconds on the x-axis. In various embodiments, the electrophoretic trace can include, for example, a lower marker (LM) and an upper marker (UM). Either or both such markers can be provided as part of a sample buffer and can be used for sample alignment. A variety of capillary electrophoresis apparatus and techniques that are suitable, or readily adaptable by those skilled in the art, for use in connection with the present teachings, are described, for example, in Capillary Electrophoresis for the Analysis of Biopolymers. By: Shen Hu; Dovichi, Norman J. Analytical Chemistry. Jun. 15, 2002, Vol. 74 Issue 12, p 2833. 18p. (AN: 7152955); incorporated herein by reference in its entirety.

Various embodiments of the present teachings contemplate the use of electrophoresis apparatus and methods such as taught in U.S. Pat. Nos. 8,778,155 and 8,784,626, as well as in U.S. Patent Application Publication No. 2015/0338347, all of which patent assets are assigned to BiOptic Inc.; and each of which is incorporated herein by reference in its entirety. U.S. Patent Publication No. 2015/0338347, for example, teaches methods for glycan profiling by capillary electrophoresis, and a capillary electrophoresis apparatus for glycan analysis (such as analysis of N-Glycans). The capillary electrophoresis apparatus uses integrated dual optical fibers for both radiation excitation and emission detection. The capillary electrophoresis apparatus is configured for performing a two-color detection for data analysis. A radiation excitation source is used to excite two emission fluorophores or dyes in the sample solution to be analyzed. One emission dye is to tag the sample and the other dye is used to provide a reference marker (e.g., a Dextran Ladder) for the sample run. Two detectors (e.g., photomultiplier tubes) are applied to simultaneously detect the fluorescent emissions from the dyes. The data collected by both detectors are processed for automated peak identification. The present teachings are well-suited for such processing, and can provide enhanced results, such as information enhanced in quality and quantity, in automated peak detection.

In various embodiments, further aspects of a system as contemplated herein can include, for example, a processing station. In accordance with various embodiments, for example, the processing station can be interfaced for communication with an electrophoresis apparatus, e.g., as described above. Such a processing station can comprise, for example, a central processing unit (CPU) and digital memory. The CPU can execute instructions in the memory for collecting and processing digital data. In some embodiments, the processing station can be integrated with the capillary electrophoresis apparatus, such as within or as a part of its housing. Alternatively, or in addition, at least a portion of the processing station can be disposed external to the electrophoresis apparatus. In various embodiments, the processing station comprises a general purpose digital computer, such as a Macintosh or PC, and/or a display-capable input-output device. In various embodiments, a human interface device (HID) can be provided comprising, for example, an externally accessible keypad, input/output unit, e.g., mouse, and one or more displays, such as an LCD or OLED display panel.

In accordance with various embodiments, one or more software programs are installed on the computing portion of the processing station, and/or on the linked computer, that can collect and analyze data. The programs can include, for example, (i) a data collection program, and (ii) a peak analysis program. In various embodiments, the data collection program can process information as it is generated, then, the peak analysis program can be run. In various alternative embodiments, the peak analysis program can run simultaneously with the data collection program. One or more emission signals can be plotted over time during or after runs. The peak analysis program determines appropriate parameters for enhancing the ascertainment of peaks. The analyzed data can be re-plotted as a series of corrected peaks representing a sequence of biomolecular units of an unknown analyte in a sample (i.e., a chromatogram or electropherogram). In some alternative embodiments, rather than performing a re-plotting step, the initial plotting of emission signals is deferred until, or subsequent to such time that a plot can be generated comprising corrected peaks. The results can be stored in a sample file, which can include, for example, raw data, electropherograms, molecular structure information, and any file information entered by the user. In some embodiments, a second file that contains text only can also be generated for each sample. This text file is suitable for use in other applications (e.g., database searches).

As discussed below, the peak analysis program can receive data comprising signal data or information detected by one or more sensors associated with the one or more capillaries. Any of various additional data or information related to the capillary electrophoresis apparatus can be detected and transmitted to the peak analysis program for purposes of enhancing the results of automated peak detection. In various embodiments of the present teachings, for example, thermocouples, potentiometers, and/or force-sensing resistors can be utilized. In some embodiments, digital sensors are employed, in some embodiments, analog sensors are utilized, and in a variety of embodiments a mix of such types of sensors are used. In various embodiments, one or more of the sensors is manufactured on a microscopic scale as micro sensors using MEMS technology. In various embodiments, a preferred sensor for use herein is substantially (i) sensitive to the measured property, (ii) insensitive to any other property potentially encountered during use, and (iii) does not influence the measured property.

In accordance with various embodiments, one or more sensors can be employed for detecting one or more respective physical properties proximate, or within the environment of each capillary. The detection can be, for example, substantially localized, and/or along or across a region. For example, in various embodiments, detection is across a region, such as longitudinally, across the length of each capillary, such as when detecting the potential across the capillary.

In various embodiments, a capillary electrophoresis apparatus according to the present teachings is equipped with at least one sensor for detecting electrical current for each capillary (herein, sometimes referred to as "current" for shorthand). The sensor can be adapted to generate a signal proportional to the detected electrical current. The electric current measures the amount of charge flowing through the separation channel (i.e., capillary bore, in the case of capillary electrophoresis.) In some embodiments, the capillary electrophoresis apparatus is equipped with at least one sensor for detecting a voltage differential across each capillary.

When used as an input variable in a method of the present teachings for increasing the yield of useful results in automated peak detection, the measured electrical current has been found to be unexpectedly beneficial. Such results can be achieved, for example, in various embodiments that use measured current, but not measured voltage differential; and, as well, such unexpected results can be achieved, in other embodiments, that use measured current as well as measured voltage differential. Importantly, the overall functionality and general usefulness of an electrophoresis apparatus can be improved, according to various embodiments of the present teachings, making use of measured current in a separation channel in the processing of data collected during an electrophoretic run. For example, according to various embodiments of such a method, methods can comprise: measuring electrical current in a separation channel, electrophoresing a sample including one or more unknown analytes along the channel, optically detecting for the one or more analytes at a detection zone of the channel, collecting detected signal data, and processing the collected signal data via a method that employs the measured current as a variable. The processing can comprise, for example, correcting for problematic issues, e.g., one or more errors, in the data during peak detection.

Figure 3:
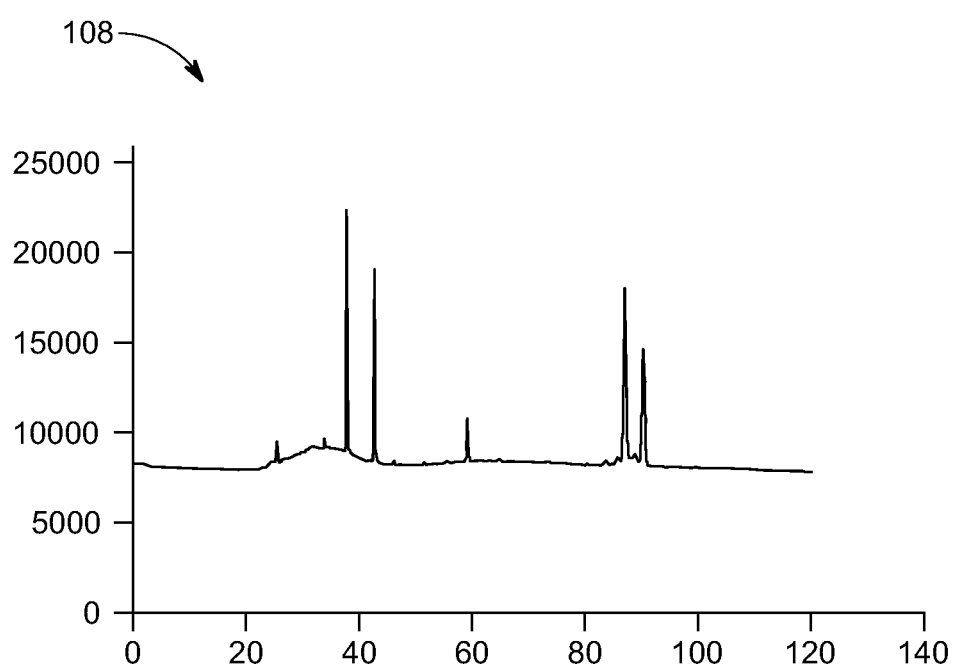
FIG. 3 Illustrates an example of electropherogram of analyte controls used as internal markers with fluorescence data on the y-axis and migration time in seconds on the x-axis from a normal separation; according to various embodiments.
Figure 4:
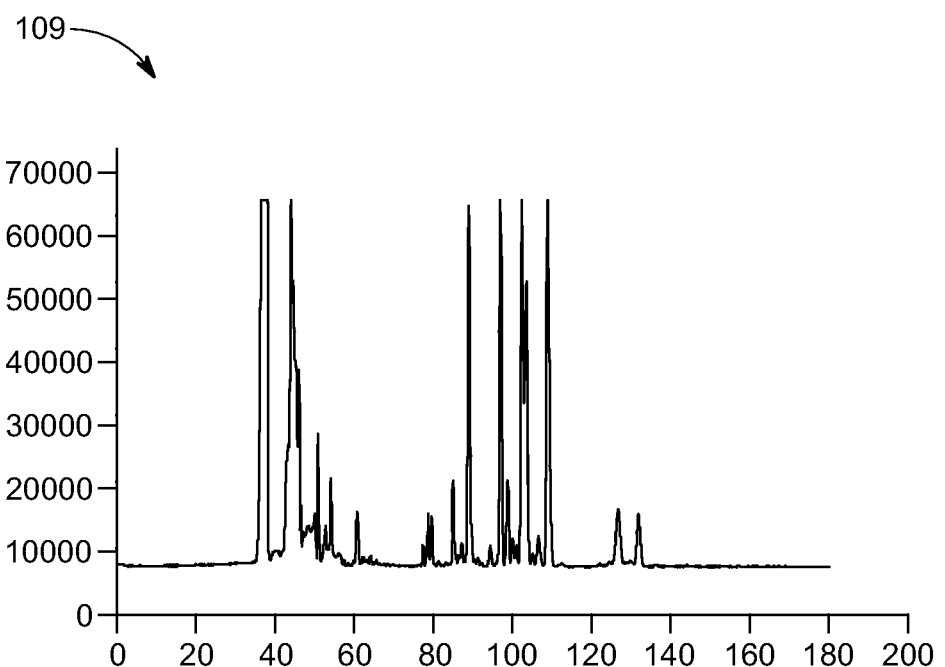
FIG. 4 Illustrates an example of electropherogram of a sample with a mixture of analytes plus analyte controls used as internal markers with fluorescence data on the y-axis and migration time in seconds on the x-axis from a normal separation; according to various embodiments.

In accordance with various embodiments, a selected electrophoresis apparatus can be used to generate signal data referred to as relative fluorescent units (RFU) as a function of time (migration time) to give a single electropherogram curve, such as shown in FIG. 1 at 104, 105 and 106 from the respective samples in 100, 101, and 102. In accordance with various embodiments, FIG. 2 shows a typical dextran (polymeric macromolecular) ladder electropherogram 107. A subset of the analytes from the ladder 107 can be isolated or synthesized to produce a set of standards or controls used in analysis. An electropherogram, such as shown in FIG. 3, at 108, of such a standard may have analytes at the start of the analyte migration time range, and at the middle and end. In accordance with various embodiments of the present teachings, analyte controls (called markers or bracketing standards) at the lower end (LBS) and upper end (UBS) of the migration time range for the analyte peaks from mixtures can be used as part of the alignment process, whereas additional analyte controls can be used as a verification device. FIG. 4 shows a typical sample electropherogram 109 with LBS and UBS markers added to the sample prior to separation.

Figure 6:
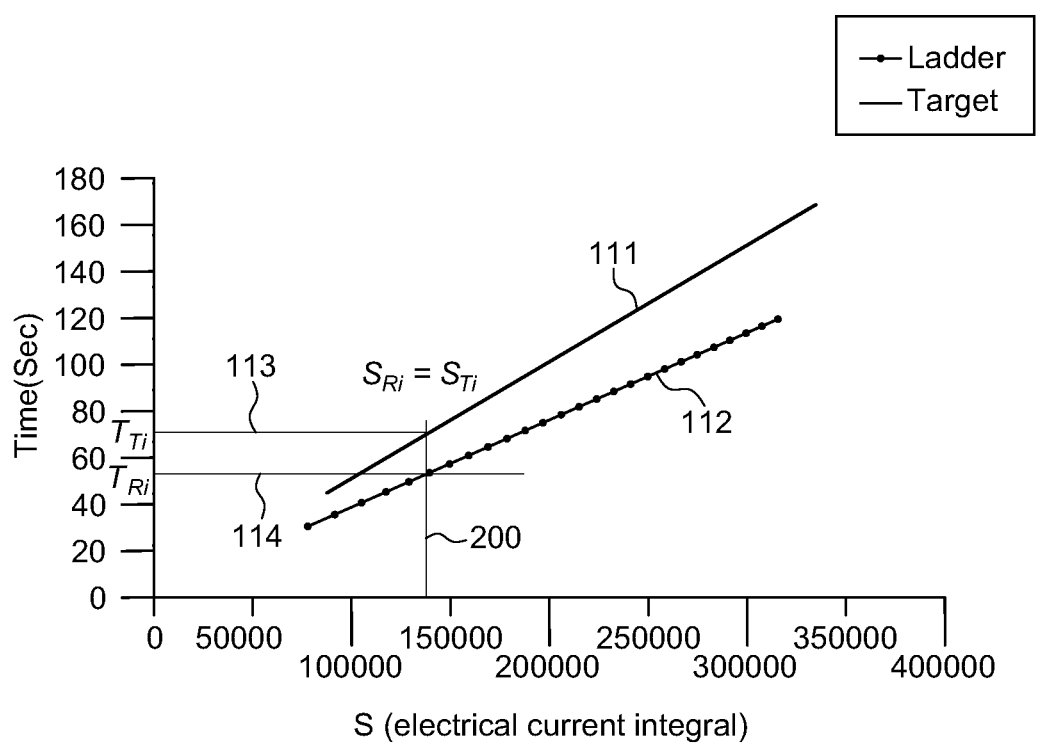
FIG. 6 Illustrates a plot from the algorithm used to perform pre-alignment current normalization; according to various embodiments.

During electrophoresis charged particles move from one electrode to the other. The movement of the particles can be affected by many factors only partially, or not related to the properties of the target particles to be measured. In accordance with various embodiments of the present teachings, a pre-alignment step or process is carried out as a means for reducing or eliminating variation caused by such factors. In various embodiments, electric current created during electrophoresis can be used to effect that correction. The electric current measures the amount of charge flowing through the conduit (capillary for example for capillary electrophoresis). Accordingly, in various embodiments, the electric current data can be employed to estimate how much charge went through from the beginning of the process to every subsequent time point of the process. Without variation, the skilled artisan would expect that the same amount of charge would flow at every time point every time the process is repeated. According to some embodiments, a way of estimating the amount of charge is for every point in the process is to add electric current values for all points prior and including the current point (sum (integral) vector). Then a plot of x, y values can be constructed, where x would be the electric current sum described above and y would be the actual time value when that sum was observed. FIG. 6, curve 111 provides an example of such a plot. Without variation in the process the skilled artisan would expect the same "sum" value to correspond to the same time for all samples. If it doesn't, it can be forced to the reference time value to produce the time that would have been obtained had there been no variation, and this comprises the pre-alignment procedure, as contemplated by various embodiments. So, in various embodiments, for every new sample, its own electric current sum for every point can be calculated and the time value for that point for that sample can be adjusted to match the time value in the virtual or physical reference sample.

Figure 5:
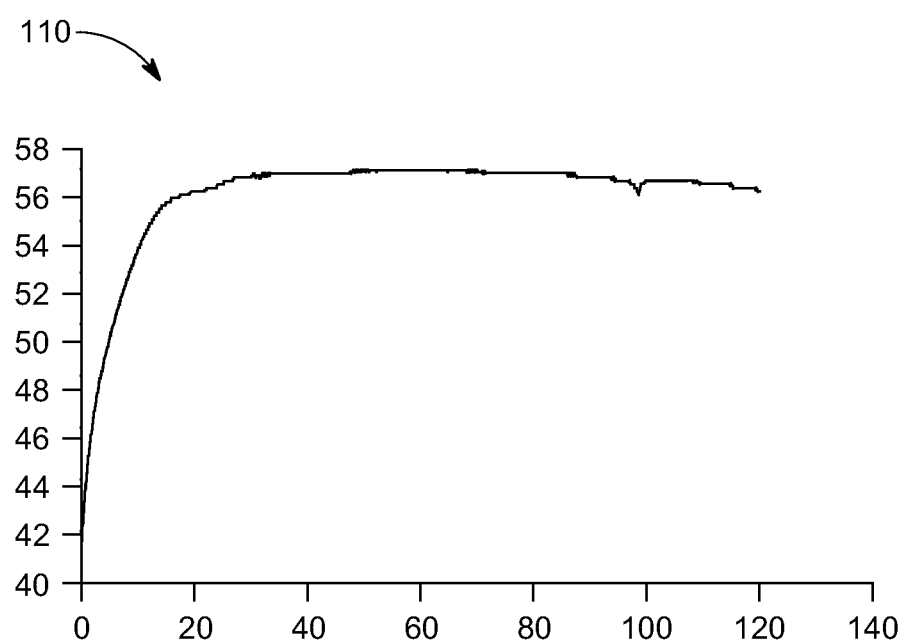
FIG. 5 Illustrates an example of the current data from the normal separation with current data on the y-axis and migration time in seconds on the x-axis from a normal separation; according to various embodiments.

FIG. 5 shows an electropherogram comprising an example of an electric current, denoted generally at 110, corresponding to the RFU separation over the migration timespan. The current data in FIG. 5 can be used, for example, to transform or normalize the migration time scale in a process referred to herein as "pre-alignment." It should be noted, however, that this terminology in no way suggests the degree or completeness of alignment resulting from this step, but instead, is used to differentiate this step from subsequent alignment processes wherein standards, such as dextran ladder and bracketing standards, are employed. In some embodiments, pre-alignment can be used to produce alignments that range from partial to complete alignment.

Various aspects of the present teachings relate to processes for the pre-aligning of data based on the individual sample measurement alone. In various embodiments, a method of performing partial or full alignment in an electrophoresis apparatus can comprise the steps of, for example:

a. combining raw separation data with electric current and optionally, electric potential data collected during the separation process in such a way to align the resulting separation data curve with one or more reference separation curves;

b. increasing or decreasing the time value for every point of the original separation data, depending on the value of the electric current at that point; and, c. optionally, increasing or decreasing the time value for every point of the original separation data depending on the value of the electric potential at that point.

Next, exemplary embodiments are described of processes and method steps for pre-aligning data based on current. A description of such steps follows.

Figure 7:
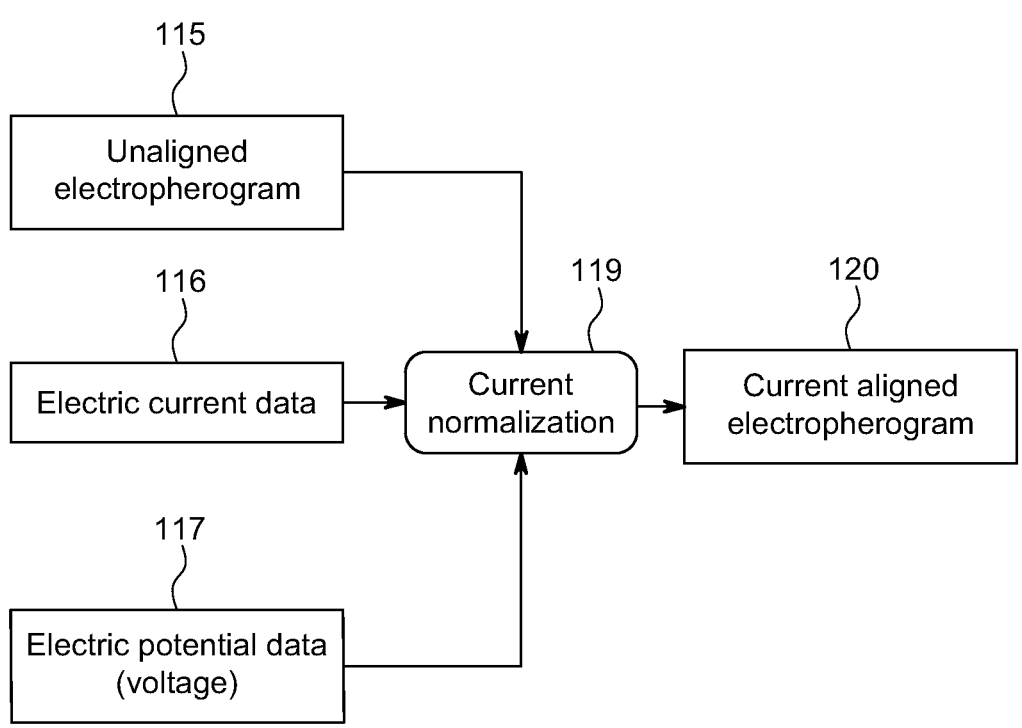
FIG. 7 Illustrates the overall process used to perform the current based normalization and transformation used in the pre-alignment process; according to various embodiments.

FIG. 6 shows an example of pre-alignment, in accordance with various embodiments, where a ladder is used to form a reference model 112, based entirely on current with no standards or controls present. (In various embodiments, the procedure can be constructed in such a way that even the ladder peak finding is not needed). According to various embodiments, this reference model can be a polynomial or cubic spline. In this example, a quadratic polynomial was used. According to various embodiments, this model 112 fits the summation (integral) of the current to migration time. Next, in various embodiments, an unknown sample can be measured and the same process can be used to compute the summation (integral) of the electric current and construct 111. In various embodiments, the electric current summation value 200 can then be input into the model 112 to give a new output (current normalized) migration time 114. In various embodiments, this conversion from the raw sample time 113 into a normalized time based on the reference ladder 114 can be used to align each subsequent injection (separation) electrophoretic data, where each unknown sample can be transformed from the original raw migration time to a common scale of the same units. FIG. 7 is a flow diagram showing the overall process of the using RFU data 115, current 116, and optionally, voltage 117 as inputs into the pre-alignment process to give aligned electropherogram data in the native migration time scale (seconds for example), in accordance with various embodiments. In various embodiments, the pre-alignment in FIG. 7 results in an x-axis in native units (seconds) in the resulting electropherogram 120, and is uniquely different from the subsequent alignment process which, as shall be seen, transforms the x-axis units at 120 into virtual units, referred to as "VU".

Ladder Calibration

Figure 8:
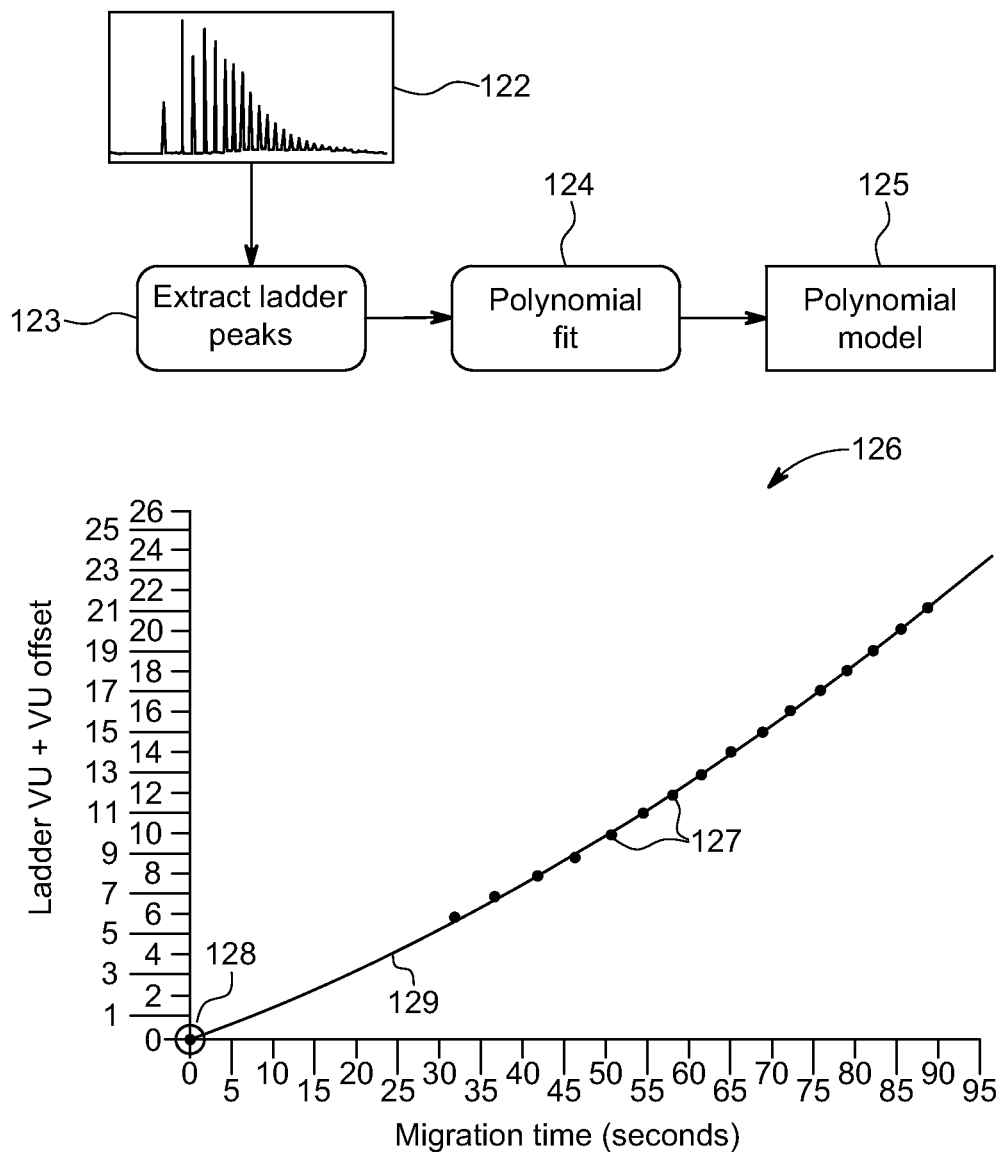
FIG. 8 Illustrates the automated process used in the macromolecular ladder calibration phase for alignment; according to various embodiments.

FIG. 8 shows an initial step in the next phase, according to various embodiments, where the overall process of a ladder calibration is shown, in this case, using either raw data or pre-aligned data as inputs. Standardized values can be allocated for observed peak-migration times of ladder components. In various embodiments, for example, the standardized values are expressed in virtual units (VU), such as macromolecule units (MU) or homopolymer units (HU). For example, a known ladder standard can comprise homopolymers of dextran the migration times for which can be expressed as glucose units (GU). In some embodiments, a known ladder standard comprises different-sized oligonucleotides the migration times for which are expressed as nucleotide units (NU). In any event, a VU value can be calculated by fitting a curve to the migration times of the ladder homopolymers. The curve can subsequently be used to assign VU values from the migration times observed for a sample comprising one or more unknown analytes.

Further in this regard, and with continuing reference to FIG. 8, ladder 122 has peaks that are detected and extracted in 123, where the migration time from each peak is matched to a virtual unit 127 corresponding to the macromolecule length of analyte in the ladder. A typical unit for the migration time comprises, for example, seconds while the semi-arbitrary virtual unit (VU) for each peak is an integer starting at 1, which increases in increments by 1 up to 15 or more (see the data on the y-axis in FIG. 8). In accordance with various embodiments, processing begins by computing an offset 128 in the polynomial 129 and determining the offset, which can then be used, in various embodiments, to translate the polynomial model 129 to give an intercept passing through the origin 128. In various embodiments, this translation offset can be stored as the VU offset for later use.

Ladder Peak Detection and Extraction

Figure 9:
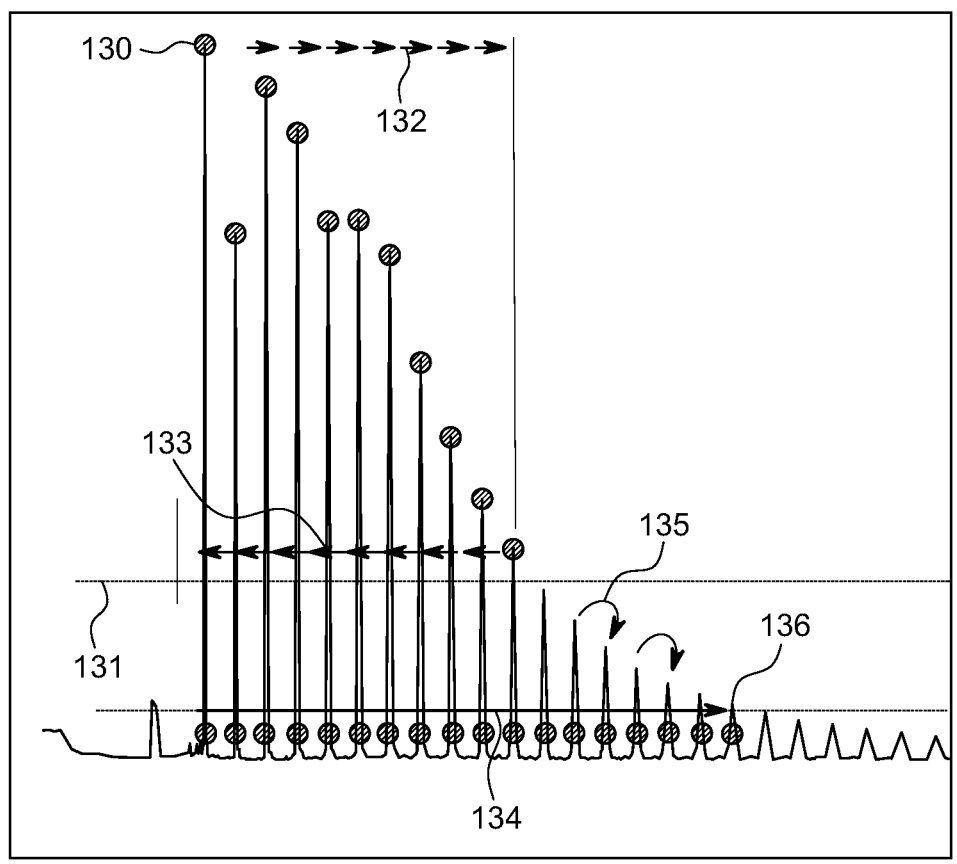
FIG. 9 Illustrates the detailed algorithm steps in the extraction of the peaks from the macromolecular ladder before the calibration phase; according to various embodiments.

FIG. 9 shows details of automated ladder peak extraction processing, according to various embodiments. In various embodiments, the highest peak 130 can be found and a relative threshold can be computed based on some acceptable percentage 131, e.g., 30% can be employed in various preferred embodiments, but the technique is not sensitive to the exact level; rather some cutoff can be used to allow the search process to terminate. In accordance with various embodiments, the search can begin with a left-to-right scan (arrows 132) of all meaningful peaks until the peak drops below the threshold 131. It is noted that a suitable definition for the term "meaningful" can be selected or devised by a person of ordinary skill in the art. For purposes of the present exemplary description, and in accordance with various embodiments of the present teachings, the term "meaningful" is defined to indicate any peak with a height>0.025*tallest peak in the electropherogram that is not saturated. For each peak in this phase, in various embodiments, the spacing can be found between consecutive peaks, then these gaps used to make a set. In various embodiments, the minimum, maximum, initial gap, average, median, and variance can be computed from this set of gaps. In various embodiments, from these statistics, lower and upper values for acceptable gaps are computed. It is noted that several methods can be used to establish the upper and lower limits, including the mean or median, plus or minus some amount of the variance. Various preferred embodiments of the present teachings employ the minimum gap from the set of all gaps as the minimum allowed gap, and a value of the first gap found in the search plus twice the value of the first change in a gap as the upper limit. In various embodiments, these lower and upper limits are based on the variations from the ladder data and not a priori gap values or fixed percentages, in order to achieve an adaptive extraction process.

In accordance with various embodiments, working backwards (arrows 133) from the rightmost peak above the threshold 131, a search is carried out for the first ladder peak, stopping once the first peak is found with a gap (migration time change from the previous peak) that is either below the lower limit or above the upper limit; in other words, if the gap is not consistent with the rest of the ladder peaks found in the first phase. Once the first ladder peak is found, in various embodiments, a new left-to-right search can be started (arrow 134), and in this case the skilled artisan would fully expect to at least return to the previous point where he or she stopped at the 30% threshold. During this traversal, in various embodiments, the peaks can be tested, for example, for abnormal drops in signal, such as where each peak cannot drop below 50% of the previous peak, which enforce continuity in the shape. In some embodiments, an optional test comprises limiting peaks from exceeding 200% of the previous peak. In various embodiments, the previously established gap test limits can be applied in this search (arrow 134). In various embodiments, once at least 10 peaks from the first peak are found, additional tests 135 can be performed, where a new gap test can be used test testing for a gap to be in the range [0.5, 1.5] of the average of the last 3 gaps. According to various embodiments, the entire extraction process can terminate once a minimum number of valid ladder peaks are found (136 being the last peak) or the peak signal drops below a meaningful level. Or, in other words, the extraction process can terminate once the last meaningful peak is found.

Model Refinement (Residual Fit)

Figure 10:
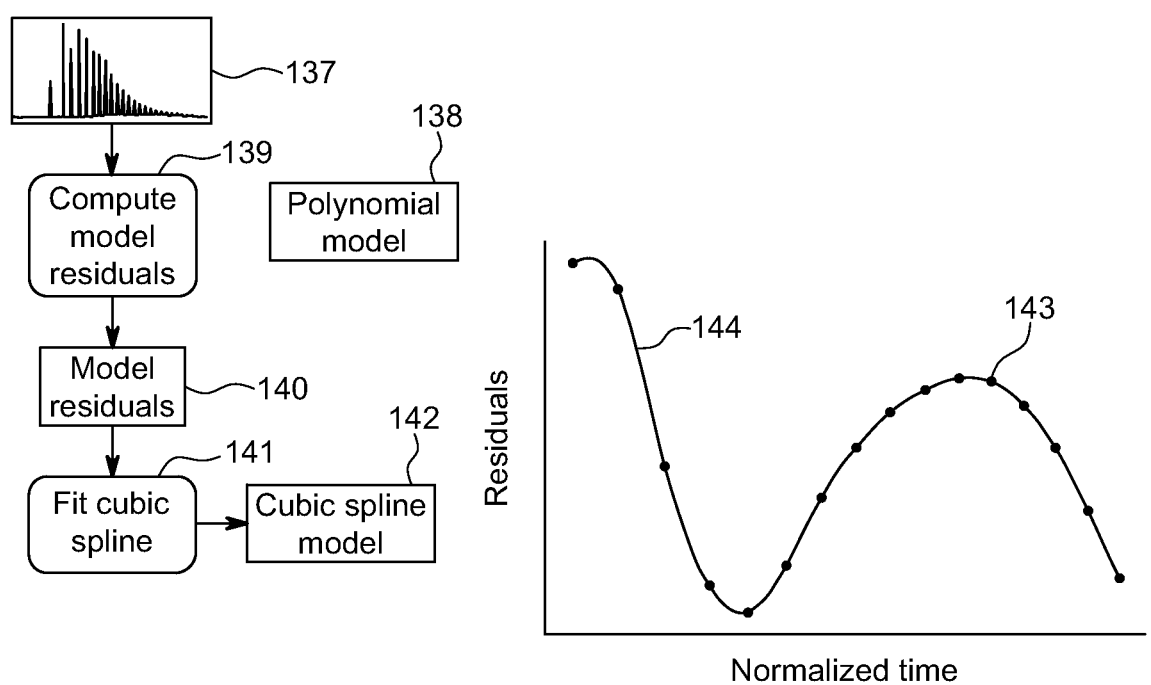
FIG. 10 Illustrates the high-level algorithm processes to build the ladder model; according to various embodiments.

As contemplated by various embodiments, FIG. 10 illustrates the algorithm flow after use of the ladder peaks to construct the base ladder quadratic model. In various embodiments, the ladder data 137 can be recycled back through the model 138 and prediction residuals 140, 143 can be computed in 139. These residuals 140, 143 can show, for example, the mismatch (time) between the data 137 and the model 138 for each peak (goodness of fit). In various embodiments, the actual residual points can be used as the input (knots 143) to a standard cubic spline, and a new cubic spline fit of the residuals can be computed in 142 to produce a new cubic spline model 144. In various embodiments, this cubic spline model 144 plus the base model 138 from the ladder can accurately represent the ladder data 137 without problems typically associated with higher order polynomial fitting near the edges of the data set. The model 144 matches the VU values at each knot. The small step size between ladder peaks and the cubic fitting in the spline can reduce distortions while providing a continuous and smooth function between known ladder control points.

Unitized Normalization

In accordance with various embodiments, a final step in FIG. 10 can comprise the unitized normalization of the x-axis time scale [0.0, 1.0] for the cubic spline model, so, for example, this component can be used in subsequent transformations.

UBS Peak Detection

Figure 11A:
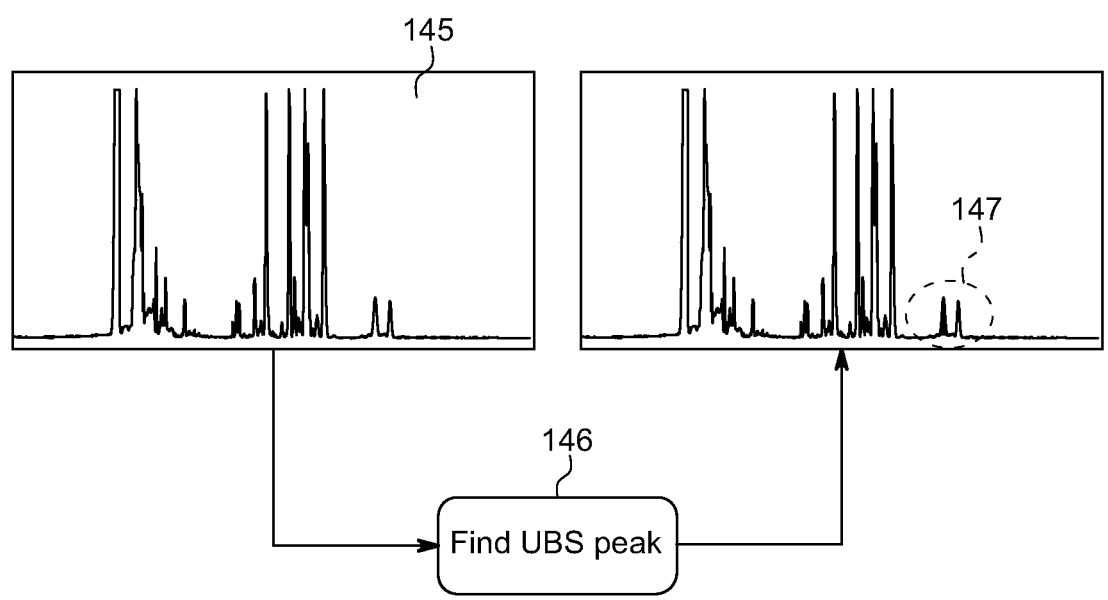
FIG. 11A Illustrates steps of searching and finding the upper bracketing standard (UBS) in unknown sample electropherograms; according to various embodiments.

In accordance with various embodiments, once the ladder model is established, such as in FIG. 11A, the algorithm can search, shown at 146, for the UBS peak 147. In various embodiments, the search process 146 examines the peaks in the unknown sample electropherogram 145, as shown in FIG. 11A. In various embodiments, this process can be based on the assumption that the UBS peak is the first meaningful peak found in a right-to-left search. Although various embodiments of this algorithm use the UBS and various preferred embodiments employ this first-come-first-serve methodology, it is noted that alternate methods can be used to find the UBS. The goal is to find a valid UBS peak. Any suitable, reliable means capable of finding a valid UBS peak, such as known to those skilled in the art, can be used.

Figure 11B:
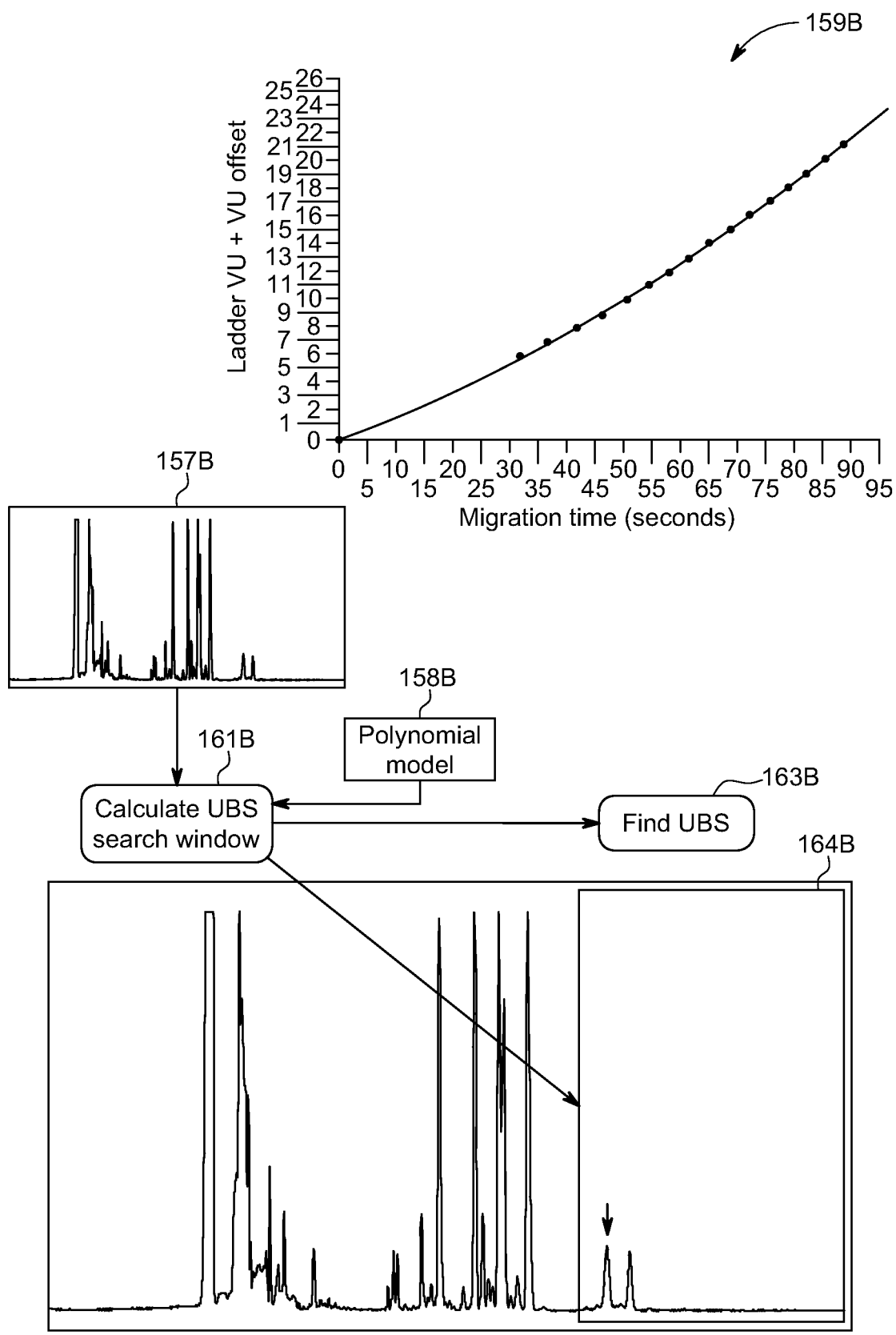
FIG. 11B illustrates the use of a polynomial model to search for the UBS; according to various embodiments.

FIG. 11B shows use of a polynomial model 159B to search for the UBS. In various embodiments, the process 161B comprises, for example, transforming the x-axis in migration time into virtualized VU so that an a priori specified UBS can be used. The rationale for using VU in this phase is to eliminate the need to know where the UBS would appear in raw migration time. From the prediction UBS location, a search window 164B is computed in VU space, where a preferred window can comprise, for example, all values greater than the expected UBS-1.0 VU. A second step 163B, which provides for finding the UBS in the window, can comprise looking for the strongest peak in the search window.

LBS Peak Detection

Figure 12:
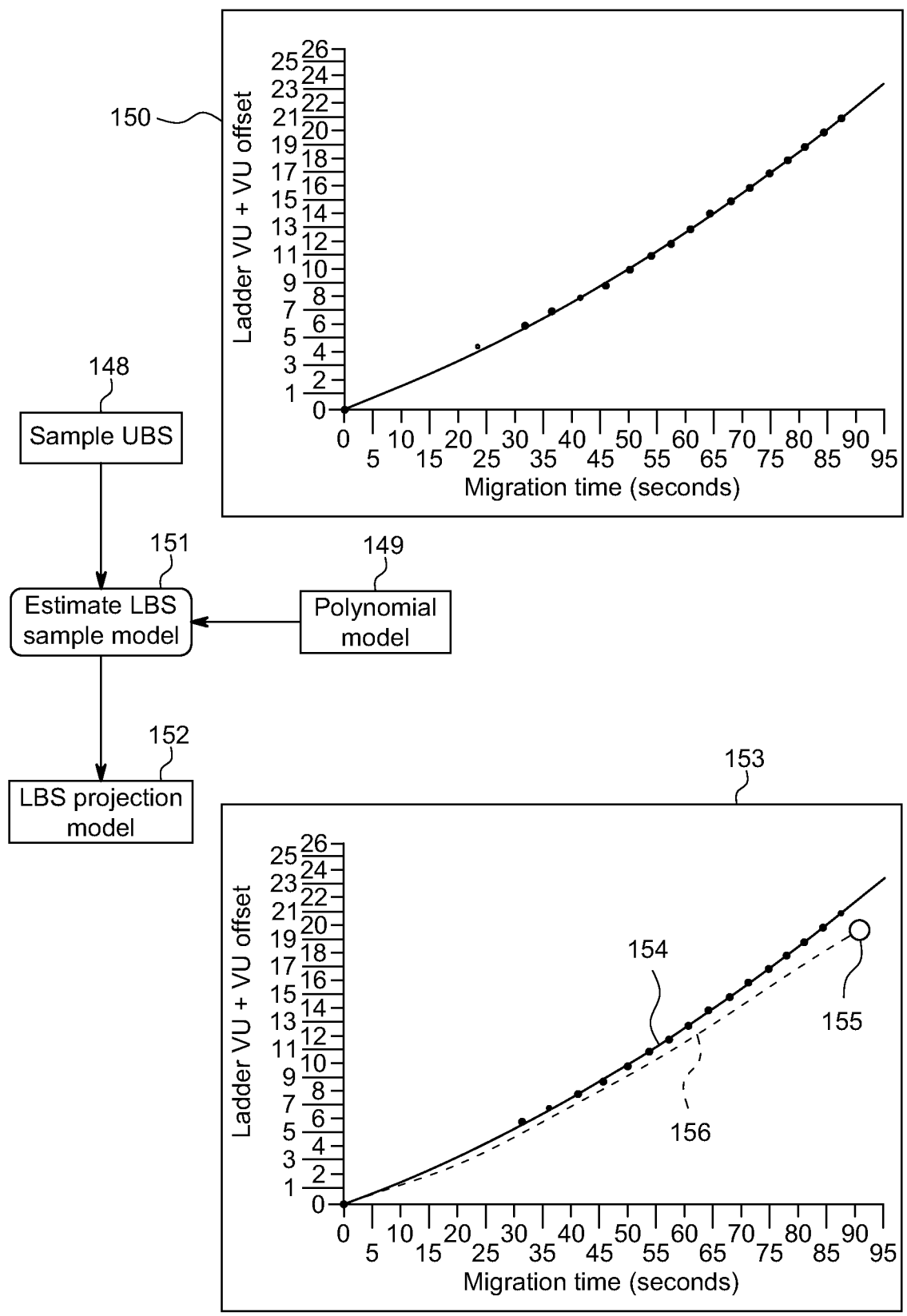
FIG. 12 Illustrates the algorithm used to bootstrap the sample model from the ladder calibration combined with the sample UBS to allow subsequent searching for the sample lower bracketing standard (LBS); according to various embodiments.
Figure 13:
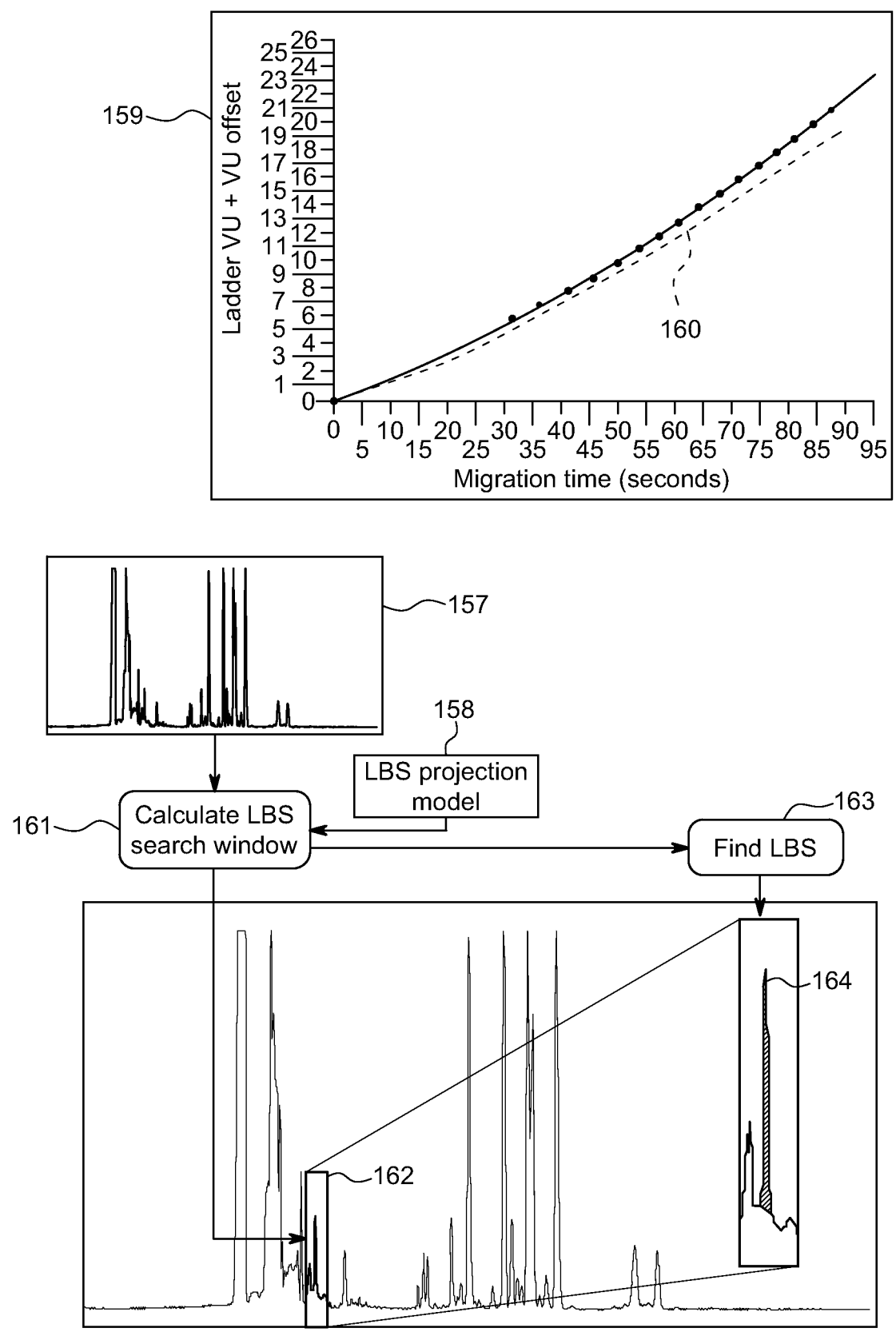
FIG. 13 Illustrates the process of finding the sample LBS; according to various embodiments.

In accordance with various embodiments, FIG. 12 shows a method of estimating (projecting) an LBS prediction model, depicted at 150, to search for the LBS using only the sample UBS, at 148, and the previous base ladder model (quadratic), at 149. In various embodiments, an object of this step is to construct a new model from the sample to find the VU region where the sample LBS is located. In various embodiments, an approach used to accomplish this can comprise modifying the ladder model using the sample UBS such that a change to the slope and curvature of equal proportions is made to the quadratic model to force a fit of the UBS sample peak. FIG. 13 shows an exemplary process to search for a sample LBS, where the sample electropherogram, depicted at 157, is input into the LBS prediction model, at 158. FIG. 13 illustrates, at 159, how the LBS prediction model 160 can be derived. The LBS model 158 is used to predict the location of the LBS in the raw sample, according to various embodiments. In various embodiments, the process 160 comprises, for example, transforming the x-axis in migration time into virtualized VU so that an a priori specified LBS can be used. In a variety of embodiments, from the predicted LBS location, a search window 161, 162 can be computed in VU space, where, in various embodiments, a preferred window comprises +/−0.5 VU. The rationale for using VU in this phase is to eliminate the need to know where the LBS would appear in raw migration time. According to various embodiments, a second step in searching for the LBS in the window can comprise looking for the strongest peak 163, 164.

Alignment

Figure 14:
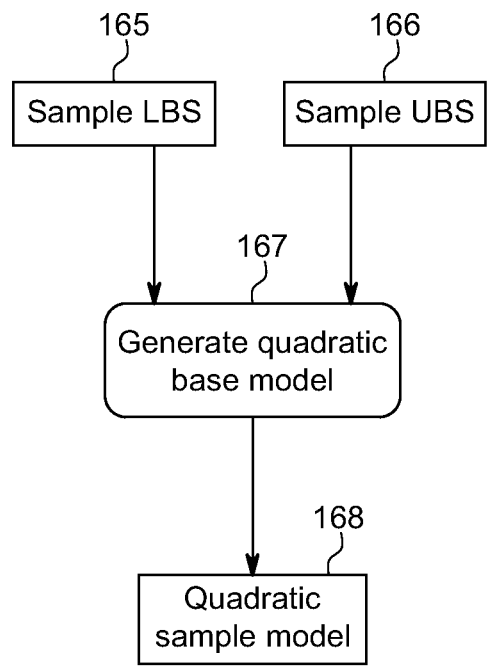
FIG. 14 Illustrates the process to generate the base (quadratic) sample model from the LBS and UBS; according to various embodiments.
Figure 14:
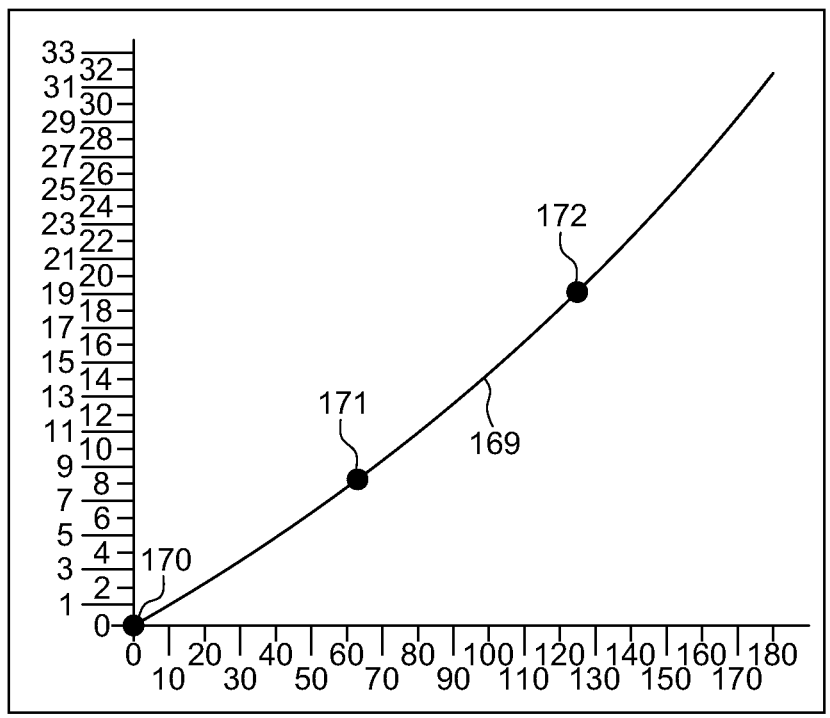
Figure 15:
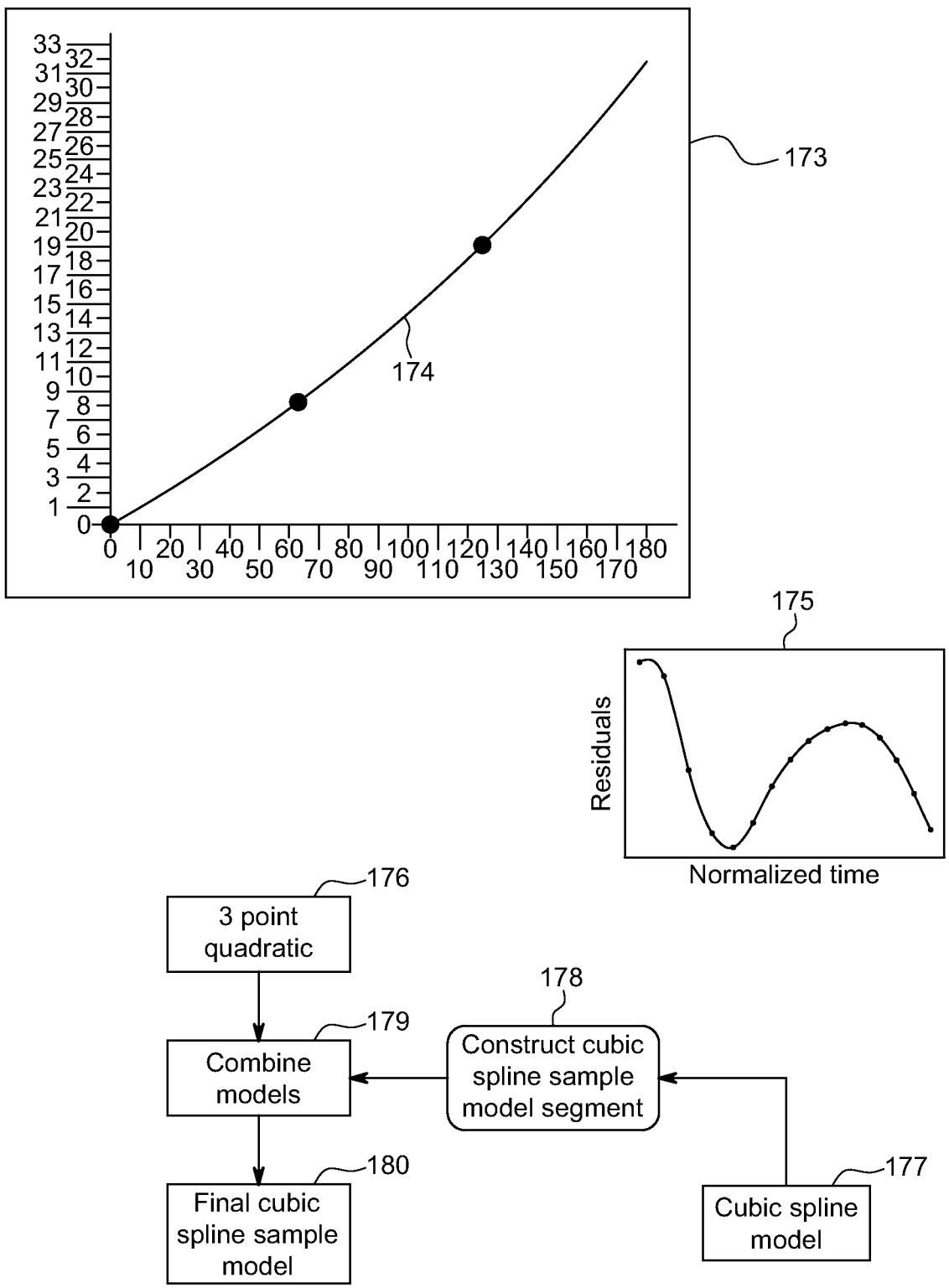
FIG. 15 Illustrates the process to splice in and merge the cubic spline component from the ladder calibration with the base (quadratic) sample model to give a final sample model for alignment; according to various embodiments.
Figure 16:
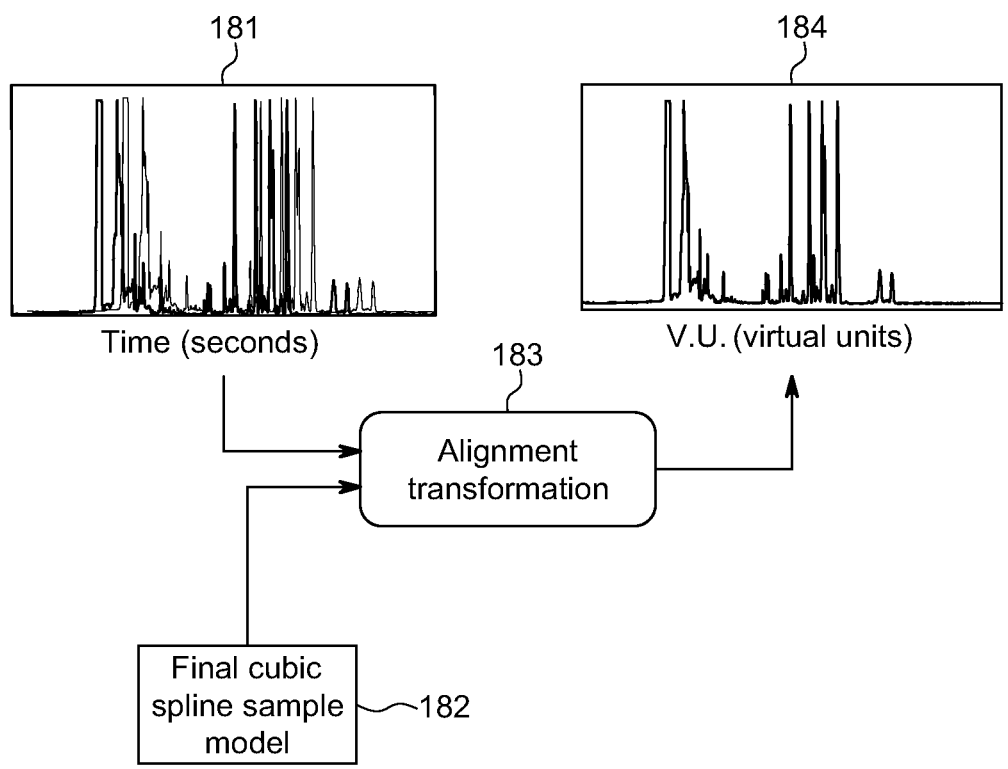
FIG. 16 Illustrates the final step of alignment where the raw or pre-aligned data is transformed into the virtualized absolute glycose unit x-axis data; according to various embodiments.

Referring to FIG. 14, an exemplary next step in the process is shown where the algorithm system uses the LBS 165, UBS 166, and computes at 167 a new sample quadratic model, at 168, through the origin 170. The LBS 171, UBS 172 and origin 170 are sufficient to generate a quadratic prediction model 169. FIG. 15 shows how this quadratic sample model 173, 174, 176 can be combined at 179 with the normalized, at 178, cubic spline component 175, 177 to produce a final sample model 180, according to various embodiments. In various embodiments, an exemplary step for use in 178, providing for realization of this combination, comprises removal of the units of the response time in the cubic spline, and normalizing the range from [0.0, 1.0], thereby allowing the component to be added directly to the sample model by matching the LBS and UBS control points. In accordance with various embodiments, the entire process can be completed, for example, as shown in FIG. 16, where the raw input data, depicted at 181, is sent to the final model, at 182, and processed, at 183, to produce aligned, virtualized VU x-axis data. According to various embodiments, the process at 183 can be based on converting the raw x-axis values from time (seconds) into VU via the final model, such as:

$$\text{FULL MODEL: } VU(i) = f_{sample}(i) + g_{unit\_vector}(i) + VU_{offset}$$

Where
i=x-axis index
f=quadratic sample model
g=cubic spline component from ladder
VU offset=constant from the intercept of the initial ladder polynomial It is noted that various embodiments of the present teachings contemplate a variety of alternate constructions; for example:

(1) $VU(i) = f_{sample}(i) + VU_{offset}$, where the cubic spline step is not used (2) $VU(i) = f2_{sample}(i) + VU_{offset}$, where the base sample model f2=the LBS projection model as shown in FIG. 12 152 and does not require nor include the LBS as shown in FIG. 13 173, 176

(3) $VU(i) = f2_{sample}(i) + g_{unit\_vector}(i) + VU_{offset}$, where the base sample model f2=the LBS projection model as shown in FIG. 12 152 and does not require nor include the LBS as shown in FIG. 13 173, 176. In this case, alternate (3) differs from (2) in that the cubic e component is used.

According to various embodiments, fourth- and lower-order polynomials are employed. For example, various embodiments provide for the use of one or more quadratic fits to manage and manipulate data systems, such as standard ladder data. Some preferred embodiments, for example, provide for the use of a quadratic polynomial curve and, in addition, an interpolating cubic-spline component to fit known-ladder data.

Figure 17:
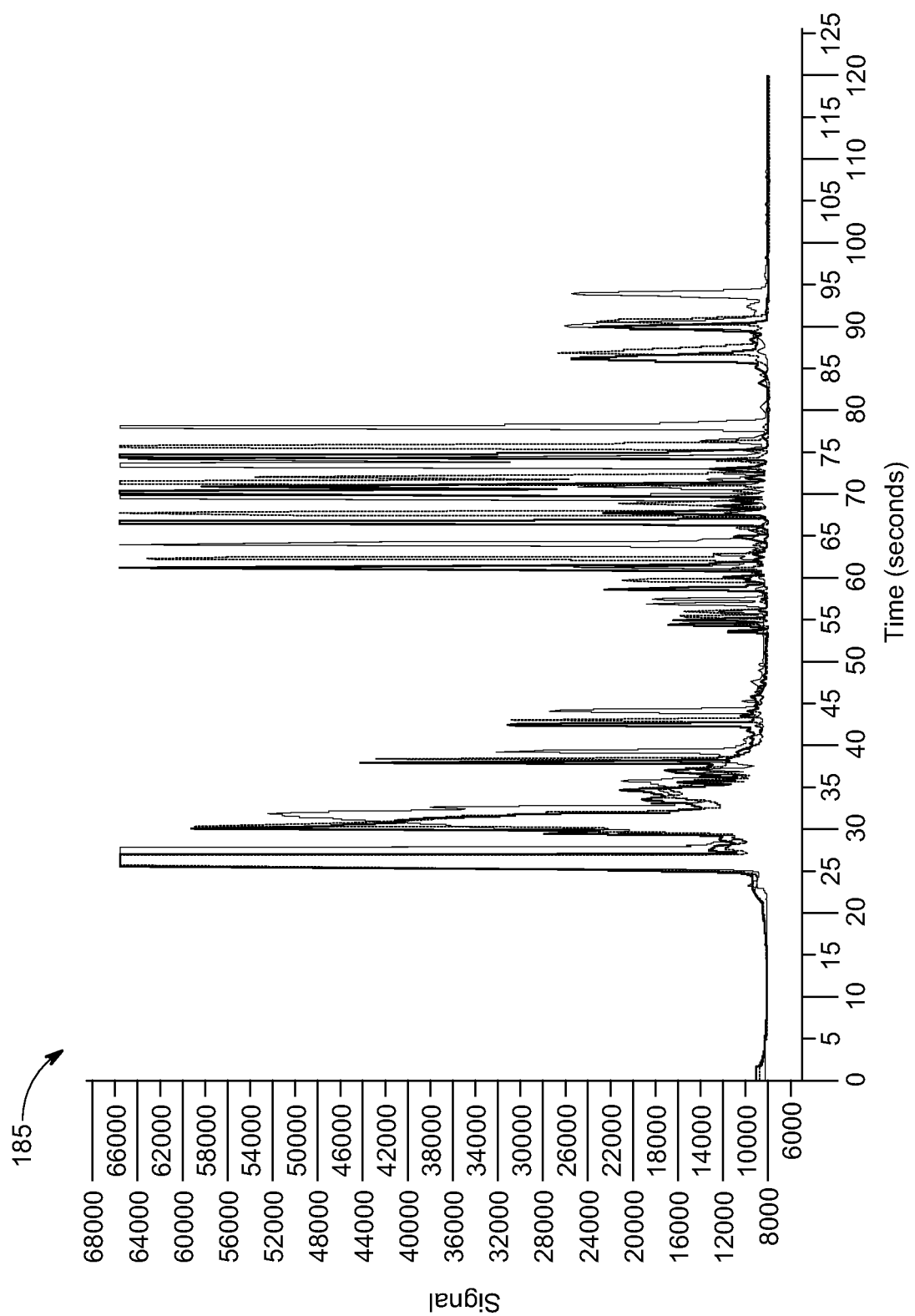
FIG. 17 Illustrates a representative example of an electropherograms from a set of glycan mixtures; according to various embodiments.
Figure 18:
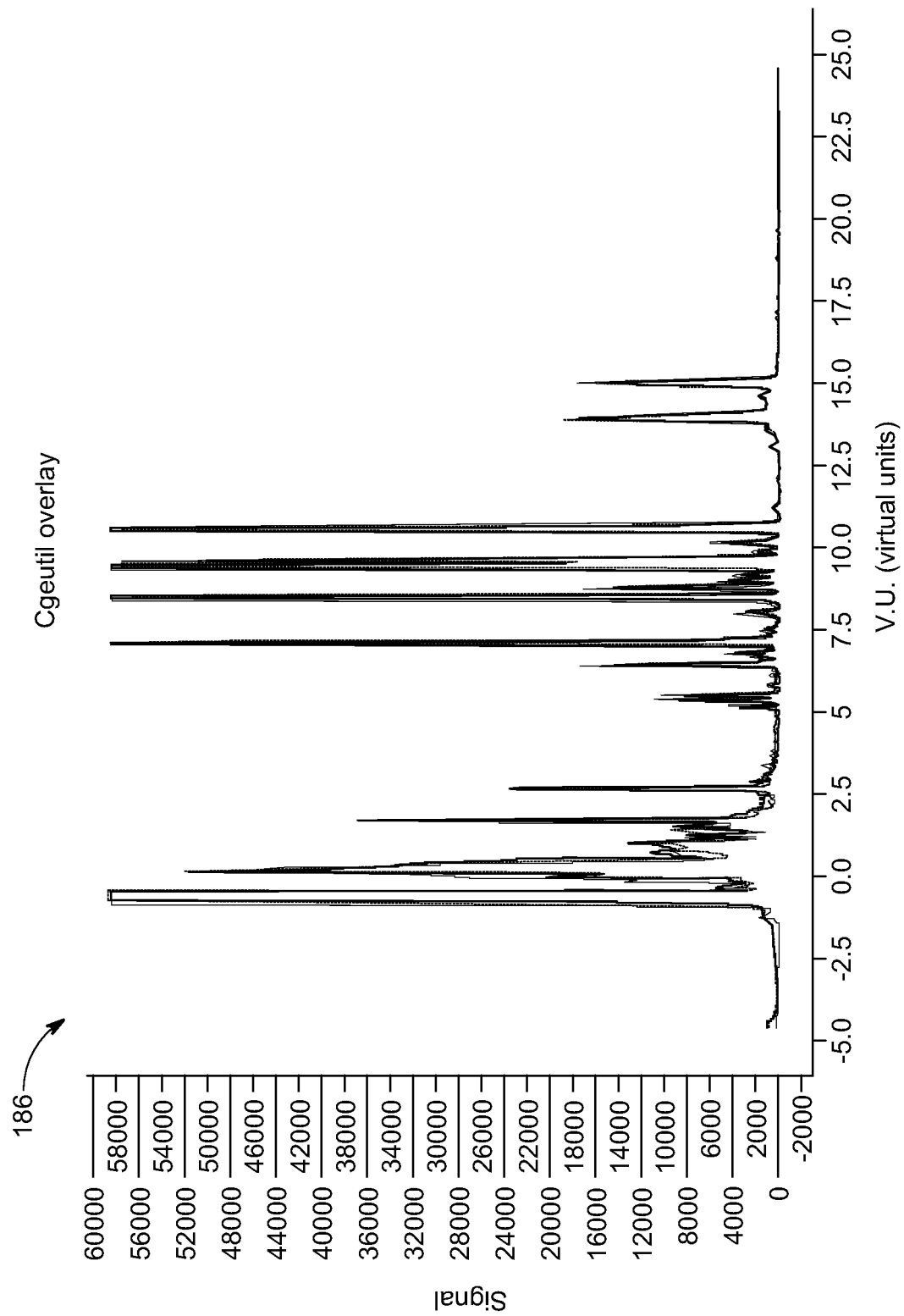
FIG. 18 Illustrates a typical set of fully transformed (virtualized, aligned) electropherograms using the raw set from FIG. 17 as inputs; according to various embodiments.
Figure 19:
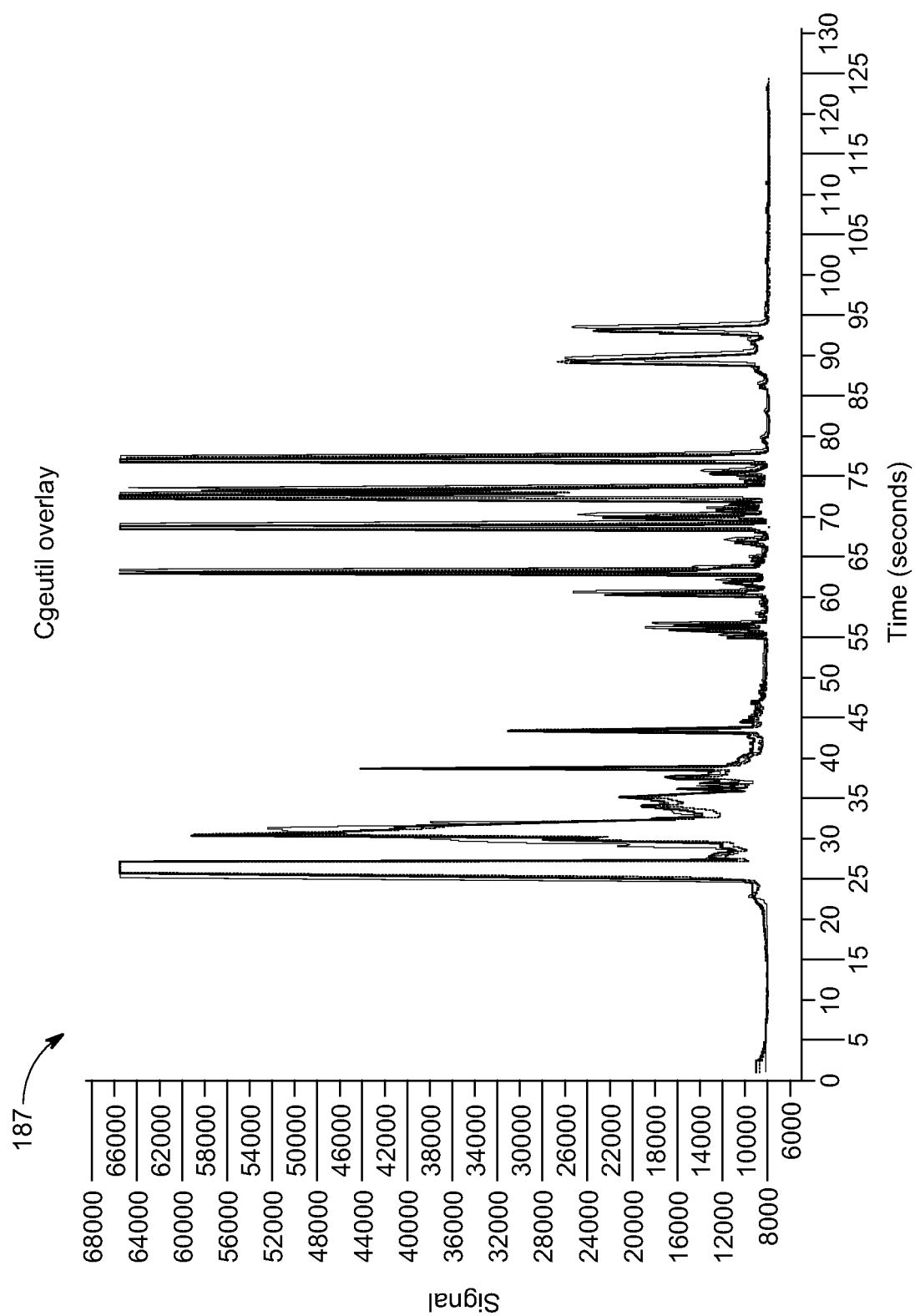
FIG. 19 Illustrates the result of the pre-alignment phase, alone, using only current; according to various embodiments.

According to various embodiments, based on the above alternate constructions, it can be shown that there exists a wide set of options in the analysis and, as such, it will be appreciated by those skilled in the art that the method of the present teachings is very flexible in practice. For example, in various embodiments, for applications that prohibit the use of the lower bracketing standard (LBS), alternate construction (2) can be appropriate and effective. In other words, for various embodiments of the present system, skipping a step can be part of the design and inherent to the power of this system. FIG. 17 shows a representative example of the electropherograms 185 from a set of glycan mixtures, according to various embodiments. FIG. 18 shows a typical set of fully transformed (virtualized, aligned) electropherograms 186 using the raw set 185 shown in FIG. 17 as inputs, according to various embodiments. In this example, the entire end-to-end process was used, starting with the pre-alignment based on current, the ladder model, sample LBS and UBS plus the cubic spline component. FIG. 19 shows the result 187 of the pre-alignment phase alone using only current, according to various embodiments.

The following example is intended for illustration purposes only, and should not be construed as limiting in any way.

Example A

An experimental setup used is shown in FIG. 1, where a block diagram shows the data collection system and the use of a dextran ladder 100, unknown glycan mixture (sample) 101 and glycan standards/controls were used.

The electrophoresis apparatus used generated signal data in relative fluorescent units (RFU) as a function of time (migration time) to give electropherogram curves as shown in 104, 105 and 106 from the respective samples in 100, 101, and 102. FIG. 2 shows a typical dextran ladder electropherogram 107. A subset of the glycans from the ladder 107 can be isolated or synthesized to produce a set of glycan standards or controls used in analysis, the electropherogram 108 (shown in FIG. 3) of such a standard may have glycans at the start of the glycan migration time range, middle and end. The glycan controls (also called markers or bracketing standards) at the lower end (LBS) and upper end (UBS) of the migration time range for the glycan peaks from mixtures are used as part of the alignment process, whereas additional glycan controls can be used as a verification device. FIG. 4 shows a typical sample electropherogram 109 with LBS and UBS markers added to the sample prior to separation.

FIG. 5 shows the electric current 110 corresponding to the RFU separation over the migration timespan. The current data in FIG. 5 was used to transform or normalize the migration time scale in a process called "pre-alignment". This pre-alignment was used to produce alignments that corrected most the variations in the data set.

FIG. 6 illustrates the process used to perform the electric current pre-alignment, where the electric current sum for every point is calculated and the time value for that point for that sample is then adjusted to match the time value in the reference sample.

Further, FIG. 6 shows the pre-alignment, where a ladder is used to form a reference model 112, based entirely on current and does not require standards or controls. This reference model was created using a quadratic polynomial fit. The model 112 fits the summation (integral) of the current to migration time. Next, an unknown glycan sample is measured and the same process is used to compute the summation (integral) of the electric current and construct 111. The electric current summation value 200 was then input into the model 112 to give a new output (current normalized) migration time 114. The conversion from the raw sample time 113 into a normalized time based on the reference ladder 114 was used to align each subsequent injection (separation) electrophoretic data, where each unknown sample is transformed from the original raw migration time to a common scale of the same units. FIG. 7 shows the overall process of using RFU data 115, current 116, and voltage 117 to give aligned electropherogram data in the native migration time scale of seconds. The pre-alignment in FIG. 7 results in an x-axis in native units (seconds) and is uniquely different from the subsequent alignment process which (as shall be shown) transforms the x-axis units into virtual units called VU.

Ladder Calibration

FIG. 8 shows the initial step in the next phase, where the overall process of a glycan ladder calibration is shown, in this case, using pre-aligned data as inputs. A ladder 122 has peaks that are detected and extracted in 123, where the migration time from each peak is matched to glycan unit (GU) 127 corresponding to the polymer or glucose unit length of dextran ladder. The migration time as measured in seconds and the GU scale starts at 1, incrementing by 1 up to 15 or more (see the data on the y-axis in FIG. 8). The initial step in the processing is to compute an offset in the quadratic polynomial 125, 126 fit of the ladder peak data 124 and determine the offset, which is then used to translate the quadratic model 129 to give an intercept passing through the origin 128, this translation offset is stored as the "GU offset" for later use.

Ladder Peak Detection and Extraction

FIG. 9 shows the details of the automated ladder peak extraction processing. The highest peak 130 is found and a relative threshold is computed based on some acceptable percentage 131, in this case, 30%. The search used a left-to-right scan (arrows 132) of all meaningful peaks until the peak height drops below the relative threshold 131. For each peak in this phase, the spacing was found between consecutive peaks, then these gaps were used to make a set. The minimum, maximum, initial gap, average, median, and variance is computed from this set of gaps. From these statistics, a lower and upper values for acceptable gaps is computed. The minimum gap was based on the set of all gaps as the minimum allowed gap, and a value of the first gap found in the search plus twice the value of the first change in a gap was uses as the upper limit. Working backwards (arrows 133) from the rightmost peak above the threshold 131, the algorithm searched for the first ladder peak, stopping once the first peak was found with a gap that was either below the lower limit or above the upper limit. Once the first ladder peak was found, a new left-to-right search was started (arrow 134). During this traversal, the peaks were tested for abnormal drops in signal, where each peak cannot drop below 50% of the previous peak. The previously established gap test limits were applied in this search (arrow 134). Once we found 10 peaks from the first peak, we performed a new gap test that required the gap to be in the range [0.5, 1.5] of the average of the last 3 gaps. The entire extraction process terminated once the ladder peaks 18 were found.

Model Refinement (Residual Lit)

FIG. 10 shows the step after the ladder peaks were used to construct the base ladder quadratic model. The ladder data 137 is recycled back through the model 138 and prediction residuals 140, 143 were computed in 139. These residuals 140, 143 show the mismatch (time) between the data 137 and the model 138 for each peak (goodness of fit). The actual residual points were used as the input (knots 143) to a standard cubic spline, and a new cubic spline fit of the residuals was computed in 142 to produce a new cubic spline model 142, 144. This cubic spline model 144 plus the base model 138 from the ladder accurately represented the ladder data with an error free representation at each node (knot) 143. The small step size between ladder peaks and the cubic fitting in the spline nearly eliminated distortions and provided a continuous and smooth function between known ladder control points.

Unitized Normalization

A final step in FIG. 10 was used for normalization of the x-axis time scale [0.0, 1.0] for the cubic spline model where the cubic spline component was used in subsequent transformations.

UBS Peak Detection

After the ladder model was established as in FIG. 10, with additional reference to FIG. 11A, the algorithm searched 146 for the UBS peak 147. The search process 146 examined the peaks in the unknown glycan sample electropherogram 145 as shown in FIG. 11A. This process was based on the assumption that the UBS peak will be the first meaningful peak found in a right-to-left search.

LBS Peak Detection

FIG. 12 shows how a LBS prediction model 150 was created to search for the LBS using only the sample UBS 148 and the previous base ladder model (quadratic) 149. The purpose of this step was to construct a new model from the sample to find where the sample LBS is located. We were able to use the sample UBS peak and adjust the slope and curvature of the ladder model in equal proportions so that the quadratic model was forced to fit our UBS sample peak. FIG. 13 shows the process used to search for the sample LBS, where a glycan sample electropherogram 157 was input into the LBS prediction model 158, 159, 160, and the LBS model 160 was used to predict the location of the LBS in the raw sample. The process 160 involved transforming the x-axis in migration time into virtualized GU so that an a priori specified LBS can be used. From the prediction LBS location, a search window 161, 162 is computed in GU space, where the preferred window is +/−0.5 GU. The rationale for using GU in this phase is to eliminate the need to know where the LBS would appear in migration time (seconds), since the location of the LBS cannot be known in advance. The second step used to find the LBS in the window involved looking for the strongest peak 163, 164.

Alignment

FIG. 14 shows the next step in the process where the algorithm system used the LBS 165, UBS 166, and computes in 167 a new sample quadratic model 168 through the origin 170. The LBS 171, UBS 172 and origin 170 were sufficient to generate a quadratic prediction model 169. FIG. 15 shows how this quadratic sample model 173, 174, 176 was combined in 179 with the normalized 178 cubic spline component 175, 177 to produce a final sample model 180. The step used in 178 allowed this combination by removing the units of the response time in the cubic spline and normalizing the range from [0.0, 1.0], thereby allow the component to be added directly to the sample model by matching the LBS and UBS control points. The entire process was completed as shown in FIG. 16, where the raw input data 181 was sent to the final model 182 and processed 183 to produce aligned, virtualized GU x-axis data. The process of 183 was based on converting the raw x-axis values from time (seconds) into GU via the final model as:

$$\text{FULL MODEL: } GU(i) = f_{sample}(i) + g_{unit\_vector}(i) + GU_{offset}$$

Where i=x-axis index f=quadratic sample model g=cubic spline component from ladder GU offset=constant from the intercept of the initial dextran ladder polynomial FIG. 17 shows a representative example of the electropherograms 185 from a set of glycan mixtures. FIG. 18 shows a typical set of fully transformed (aligned) electropherograms 186 using the raw set 185 shown in FIG. 17 as inputs. In this example, the entire end-to-end process was used, starting with the pre-alignment based on current, the ladder model, sample LBS and UBS plus the cubic spline component. FIG. 19 shows the result 187 of the pre-alignment phase alone using only current.

Example B

In subparts (1) through (5) to this example, set out below, exemplary protocols are provided, in which:

EC—electric current;

RM—reference model; and

Conduit=analyte conduit—the conduit through which the analyte moves during electrophoresis, such as a longitudinal bore of a capillary, e.g., as with capillary electrophoresis.

Example B, Subpart (1)

1. An exemplary protocol is provided for performing partial or full alignment using electric current and electric potential data for electrophoresis systems using a reference curve, comprising the steps:
   1.1. The following actions can be performed during the separation process for each sample.
      1.1.1. Measure separation (graph 108, FIG. 3).
      1.1.2. Measure or estimate the potential between the ends of the conduit.
      1.1.3. Measure or estimate the electric current flowing through the conduit under the influence of an electric field (graph 110, FIG. 5).
      1.1.4. Record the time of every measurement.
   1.2. Collect the measurements described in [1.1] for multiple samples. The samples may include unknown samples and ladder samples.
   1.3. Select a reference sample and construct a mathematical model using the electric current data and electric potential data.
      1.3.1. Calculate sampling period normalization factor for the collected EC data (see, graph 110, FIG. 5) by dividing the actual sampling period (seconds) by an arbitrary reference sampling period (seconds).
      1.3.2. Calculate EC integral vector using collected EC data (see, graph 110, FIG. 5) where each element of the vector is the sum of the previous element and EC value at the current point multiplied by the sampling period normalization factor.
  1.3.3. Perform optional electric potential normalization using collected electric potential data by dividing each element in the calculated EC integral vector by the electric potential (volts) at that measurement point.
  1.3.4. Construct a time vector (T) using recorded time in such a way that there is a time value Ti available for every Si (EC integral) value calculated above.
  1.3.5. Construct the reference model that will relate S (EC integral) values calculated above to T (time) values. One method comprises using a quadratic fit of the (S, T) points where S is the input (independent variable) and T the output (dependent variable). That equation can be designated as the reference model (RM). Alternative polynomial models can be used to achieve a comparable result therefore this method is not limited to a quadratic. An example of the resulting reference EC curve is 112, FIG. 6.
 1.4. Align target electropherograms using the reference model (RM) calculated in [1.3.5] (See FIG. 6 for the steps below).
  1.4.1. Construct the EC integral vector for the target curve using steps [1.3.1), [1.3.2] and optionally [1.3.3] above. The result is 111, FIG. 6.
  1.4.2. For every time $T_{Ti}$ of the target curve, find corresponding EC value $S_{Ti}$ of the target curve.
  1.4.3. Substitute S in RM (Equation 1.4) with $S_{Ti}$ and calculate $T_{Ri}$. FIG. 6 is a graphical representation of finding the new time value for the target curve.
  1.4.4. $T_{Ri}$ is the new time of point i of the target curve.

Example B, Subpart (2)

2. An exemplary protocol is provided for performing partial or full alignment using elect current and electric potential data for electrophoresis systems using a reference ladder, comprising the steps:
 2.1. The following actions can be performed during the separation process for each sample.
  2.1.1. Measure separation (graph 108 in FIG. 3).
  2.1.2. Measure or estimate the potential between the ends of the conduit.
  2.1.3. Measure or estimate the electric current flowing through the conduit under the influence of an electric field (graph 110, FIG. 5).
  2.1.4. Record the time of every measurement.
 2.2. Collect the measurements described in [2.1] for multiple samples. The samples may include unknown samples and ladder samples.
 2.3. Select a reference sample and construct a mathematical model using the electric current data and electric potential data.
  2.3.1. Calculate sampling period normalization factor for the collected EC data (graph 110, FIG. 5) by dividing the actual sampling period (seconds) by an arbitrary reference sampling period (seconds).
  2.3.2. Calculate EC integral vector using collected EC data (graph 110, FIG. 5) where each element of the vector is the sum of the previous element and EC value at the current point multiplied by the sampling period normalization factor.
  2.3.3. Perform optional electric potential normalization using collected electric potential data by dividing each element in the calculated EC integral vector by the electric potential (volts) at that measurement point.
  2.3.4. Perform ladder peak extraction using the collected separation data (graph 107 in FIG. 2) by selecting a single point on the time axis to represent the peak location. Construct an array of (S, T) points where S is the EC integral value for each peak and T is time in seconds for each peak.
  2.3.5. Construct the reference model that will relate S (EC integral) values calculated above to T (time) values. A preferred method involves using a quadratic fit of the (S, T) points where S is the input (independent variable) and T the output (dependent variable). Let's call that equation the reference model (RM). Alternative polynomial models can be used to achieve a comparable result therefore this method is not limited to a quadratic. An example of the resulting reference EC curve is 112, FIG. 6.
 2.4. Align target electropherograms using the reference model (RM) calculated in [2.3.5] (See FIG. 6 for the steps below).
  2.4.1. Construct the EC integral vector for the target curve using steps [2.3.1], [2.3.2] and optionally [2.3.3] above. The result is 111, FIG. 6.
  2.4.2. For every time $T_{Ti}$ of the target curve, find corresponding EC value $S_{Ti}$ of the target curve.
  2.4.3. Substitute S in RM (Equation 1.4) with $S_{Ti}$ and calculate $T_{Ri}$. FIG. 6 is a graphical representation of finding the new time value for the target curve.
  2.4.4. $T_{Ri}$ is the new time of point i of the target curve.

Example B, Subpart (3)

3. An exemplary protocol is provided for performing partial or full alignment using electric current and electric potential data for electrophoresis systems using a reference curve without constructing RM, comprising the steps:
 3.1. The following actions can be performed during the separation process for each sample.
  3.1.1. Measure separation (graph 108 in FIG. 3).
  3.1.2. Measure or estimate the potential between the ends of the conduit.
  3.1.3. Measure or estimate the electric current flowing through the conduit under the influence of an electric field (graph 110, FIG. 5).
  3.1.4. Record the time of every measurement.
 3.2. Collect the measurements described in [3.1] for multiple samples. The samples may include unknown samples and ladder samples.
 3.3. Select a reference sample and construct a mathematical model using the electric current data and electric potential data.
  3.3.1. Calculate sampling period normalization factor for the collected EC data (graph 110, FIG. 5) by dividing the actual sampling period (seconds) by an arbitrary reference sampling period (seconds).
  3.3.2. Calculate EC integral vector using collected EC data (graph 110, FIG. 5) where each element of the vector is the sum of the previous element and EC value at the current point multiplied by the sampling period normalization factor. An example of the resulting reference EC curve is 112, FIG. 6.
  3.3.3. Perform optional electric potential normalization using collected electric potential data by dividing each element in the calculated EC integral vector by the electric potential (volts) at that measurement point.
    3.3.4. Construct a time vector (T) using recorded time in such a way that there is a time value Ti available for every Si (EC integral) value calculated above.
  3.4. Align target electropherograms using the reference EC integral vector and the time vector calculated in (3.3) (See FIG. 6 for the steps below).
    3.4.1. Construct the EC integral vector for the target curve using steps [3.3.1], [3.3.2] and optionally [3.3.3] above. The result is 111, FIG. 6.
    3.4.2. For every time $T_{Ti}$ of the target curve, find corresponding EC value $S_{Ti}$ of the target curve.
    3.4.3. Find the point in $S_R$ where $S_{Ri}=S_{Ti}$ and then find $T_{Ri}$ that corresponds to that point. FIG. 6 is a graphical representation of finding the new time value for the target curve.
    3.4.4. $T_{Ri}$ is the new time of point i of the target curve.

Example B, Subpart (4)

4. An exemplary protocol for the reference curve selection for performing partial or full alignment using electric current and electric potential data for electrophoresis systems as in subparts (1), (2), and (3), above, comprising the steps:
  4.1. The reference curves described in subparts (1), (2) and (3), above, can be selected from or more curves a si run and used during the same run.
  4.2. The reference curves described in subparts (1), (2), and (3), above, can be selected from one or more curves in a single run and saved to be used in other runs for the same system instrument).
  4.3. The reference curves described in subparts (1), (2), and (3), above, can be selected from one or more curves in a single run and saved to be used in other runs for other systems (instruments).
  4.4. The reference curves described in subparts (1), (2), and (3), above, can be selected from one or more curves from one or more runs from one or more instruments and saved for future use.

Example B, Subpart (5)

5. An exemplary protocol for the reference model selection for performing partial or full alignment using electric current and electric potential data for electrophoresis systems described in subparts (1) and (2), above, comprising the steps:
  5.1. The reference model (RM) described in subparts (1) and (2), above, can be constructed using a reference sample or a ladder from the same plate and run as the target samples being aligned.
  5.2. The reference model (RM) described in subparts (1) and above, can be constructed using a reference sample or a ladder from one plate or run and plied to target curves from a different plate or run.
  5.3. The above mentioned reference model (RM) can be calculated every time it's needed from the reference curve or saved and reused every time it's needed.

All references set forth herein are expressly incorporated by reference in their entireties for all purposes.

Those skilled in the art can now appreciate from the foregoing description that the broad teachings herein can be implemented in a variety of forms. Therefore, while the present teachings have been described in connection with various embodiments and examples, the scope of the present teachings are not intended, and should not be construed to be, limited thereby. Various changes and modifications can be made without departing from the scope of the present teachings.

The invention claimed is:

1. A system comprising:
  a separation channel comprising a separation medium;
  a power source for applying a potential across the separation channel to cause a sample to migrate therealong;
  a detector for measuring signal intensity associated with a sample migrating along the separation channel as a function of time; and
  a computing portion comprising a computer-readable medium containing software code embodying executable instructions for:
    receiving a first set of data comprising a plurality of signal peaks over time corresponding to an electrophoretic separation of a known ladder standard
    allocating respective standardized values, expressed in virtual units, for the peak-migration times, the virtual units corresponding to peak-migration times of ladder components of the known ladder standard;
    fitting a polynomial curve to the ladder standard, thereby generating a first polynomial model; and
    determining an offset from the origin in the first polynomial model.

2. The system of claim 1, wherein the separation channel comprises a longitudinal bore of an elongate capillary tube.

3. The system of claim 1, wherein the polynomial curve comprise fourth- or lower-order polynomial curve.

4. The system of claim 1, wherein the known ladder standard comprises dextran and the virtual units comprise glucose units.

5. The system of claim 1, the computer-readable medium containing software code further comprising executable instructions for:
  translating the first polynomial model, using the offset, to pass through the origin, thereby generating a translated first polynomial model, and
  recycling the first data set back through the first polynomial model and determining at least two prediction residuals, wherein the residuals reveal the extent of mismatch, in time, between the received and modelled peaks.

6. The system of claim 5, the computer-readable medium containing software code further comprising executable instructions for:
  fitting a cubic spline curve to the residuals, thereby generating a cubic-spline model component,
  receiving a second set of data comprising one or more peaks over time corresponding to an electrophoretic separation of a mixture comprising (a) an unknown analyte, (b) an upper bracketing standard, and (c) a lower bracketing standard,
  determining a peak for the upper bracketing standard, and
  adjusting the slope and curvature of the translated first polynomial model in equal proportions to the upper bracketing standard, thereby generating an upper bracketing standard model.

7. The system of claim 6, the computer-readable medium containing software code comprising executable instructions for:
  determining a peak for the lower bracketing standard using the upper bracketing standard model, fitting a polynomial curve to the lower bracketing standard, the upper bracketing standard, and the origin, thereby generating a second polynomial model, combining (a) the second polynomial model, (b) the cubic spline model component, and (c) the offset, thereby generating a final reference model, and transforming the second set of data into virtual units using the final reference model.

8. A system comprising:

a separation channel comprising a separation medium, a power source for applying a potential across the channel to cause a sample to migrate therealong, a detector for measuring signal intensity associated with a sample migrating along the channel as a function of time; and a computing portion comprising a computer-readable medium containing software code embodying executable instructions for:

receiving a first set of data comprising a plurality of signal peaks over time corresponding to an electrophoretic separation of a known ladder standard, allocating respective standardized values, expressed in virtual units, for the peak- migration times, the virtual units corresponding to peak-migration times of ladder components of the known ladder standard, fitting a polynomial curve to the ladder standard, thereby generating a first polynomial model, determining an offset from the origin in the first polynomial model, translating the first polynomial model, using the offset, to pass through the origin, thereby generating a translated first polynomial model, receiving a second set of data comprising one or more peaks over time corresponding to an electrophoretic separation of a mixture comprising (a) one or more respective unknown analytes, (b) an upper bracketing standard, and (c) a lower bracketing standard, determining a peak for the upper bracketing standard, adjusting the slope and curvature of the translated first polynomial model in equal proportions to the upper bracketing standard, thereby generating an upper bracketing standard model, determining a peak for the lower bracketing standard using the upper bracketing standard model, fitting a polynomial curve to (a) the upper bracketing standard, (b) the lower bracketing standard, and (c) the origin, thereby generating a second polynomial model, combining the second polynomial model and the offset, thereby generating a final reference model, and transforming the second set of data into virtual units using the final reference model.

9. The system of claim 8, wherein the polynomial curves comprise fourth- or lower-order polynomial curves.

10. The system of claim 8, wherein the known ladder standard comprises dextran and the virtual units comprise glucose units.

11. A method comprising:

applying a potential across a separation channel to generate a current therein and to separate a sample comprising an unknown analyte in the channel so that an electropherogram of a signal as a function of time is produced, during the separation, measuring the current between the ends of the channel as a function of time, integrating the current with respect to time to provide a cumulative current as a function of time, using a reference standard, constructing a reference model that relates cumulative current values to migration time values, and using the reference model, adjusting observed migration time values for the sample to current normalized time values to generate an aligned the electropherogram for the sample.

12. The method of claim 11, further comprising:

identifying peaks in the electropherogram that correlate with the unknown analyte in the sample.

13. The method of claim 11, wherein a quadratic polynomial fit is used to construct the reference model.

14. The method of claim 11, further comprising:

further aligning the current-normalized time values using one or more additional reference models that relate the current-normalized time values to standardized virtual units corresponding to peak-migration times of ladder components of a known ladder standard.

15. The method of claim 14, wherein the one or more additional reference models are constructed using a ladder standard and at least one bracketing standard.

16. A method for aligning data from an separation of a sample mixture, comprising the steps:

(a) performing an initial alignment on raw sample data using a first reference model that relates peak-migration time values to cumulative current values, and (b) performing a second alignment on the data aligned in step (a) using one or more additional reference models that relate the data aligned in step (a) to standardized virtual units corresponding to peak-migration times of ladder components of a known ladder standard.

17. The method of claim 16, wherein the one or more additional reference models are constructed using a ladder standard and at least one bracketing standard.

18. The method of claim 17, wherein the bracketing standard comprises a portion of the sample mixture.

19. The method of claim 17, wherein the second reference model is constructed using an upper bracketing standard.

20. The method of claim 19, wherein the second reference model is constructed further using a lower bracketing standard.

* * * * *